United States Patent
Menta et al.

(10) Patent No.: US 6,753,342 B2
(45) Date of Patent: Jun. 22, 2004

(54) 2-(1H-INDOL-3-YL)-2-OXO-ACETAMIDES WITH ANTITUMOR ACTIVITY

(75) Inventors: Ernesto Menta, Monza (IT); Nicoletta Pescalli, Monza (IT)

(73) Assignee: Novuspharma S.p.A., Milan (IT)

( * ) Notice: Subject to any disclaimer, the term of this patent is extended or adjusted under 35 U.S.C. 154(b) by 73 days.

(21) Appl. No.: 10/149,406

(22) PCT Filed: Dec. 21, 2000

(86) PCT No.: PCT/EP00/13068

§ 371 (c)(1), (2), (4) Date: Sep. 18, 2002

(87) PCT Pub. No.: WO01/47916

PCT Pub. Date: Jul. 5, 2001

(65) Prior Publication Data

US 2003/0158153 A1 Aug. 21, 2003

(30) Foreign Application Priority Data

Dec. 23, 1999 (IT) .......................... MI99A2693

(51) Int. Cl.$^7$ ..................... A61K 31/404; C07D 209/04
(52) U.S. Cl. ..................... 514/414; 548/465; 546/278.1
(58) Field of Search .................. 548/465; 514/414; 546/278.1

(56) References Cited

U.S. PATENT DOCUMENTS 6,100,283 A * 8/2000 Griffin et al. ............... 514/394
6,251,923 B1 * 6/2001 Hofgen et al. ............... 514/339

FOREIGN PATENT DOCUMENTS

WO  99/12917  3/1999
WO  99/51224  10/1999

* cited by examiner

*Primary Examiner*—Joseph K. McKane
*Assistant Examiner*—Golam M M Shameem
(74) *Attorney, Agent, or Firm*—Rothwell, Figg Ernst & Manbeck

(57) ABSTRACT

2-(1H-Indol-3-yl)-2-oxo-acetamides having antitumor activity, in particular against solid tumors, more precisely colon and lung tumors, of the following formula I: wherein Y is an oxygen of sulfur atom and X, $R_1$, $R_2$, $R_3$, $R_4$ and $R_5$ are as defined in claim 1.

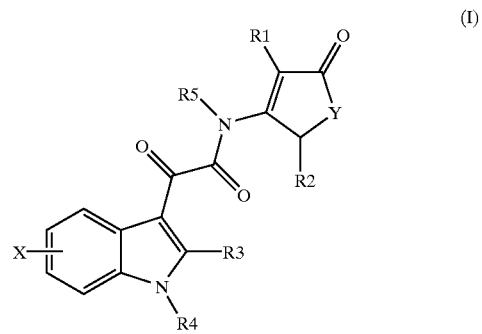

5 Claims, No Drawings

2-(1H-INDOL-3-YL)-2-OXO-ACETAMIDES WITH ANTITUMOR ACTIVITY

The present invention relates to 2-(1H-indol-3-yl)-2-oxo-acetamides having antitumor activity, particularly against solid tumors, more precisely colon and lung tumors.

Colo-rectal carcinoma is one of the most common tumors in Western countries as it accounts for about 421,000 new cases each year in the world, and it is the most frequent cause of death, except lung and breast cancers.

Surgical cure is possible in about 40–50% of patients, the remaining patients can be treated with combined chemotherapy, to obtain complete remission in a percentage not higher than 5%.

Colo-rectal tumors are usually refractory or poorly sensitive to the presently available chemotherapy, and the only agent who has some efficacy for this type of cancer is 5-fluorouracil.

No therapeutical alternatives are at present available in case of failure of the combination chemotherapy based on 5-FU. There is therefore strong need for novel medicaments active against this type of tumors.

WO 99712917 in the name of Roche Diagnostics discloses 4-ureido and thioureido 2(5H)-furanone or 2(5H)-thiophenone derivatives with antitumor activity, particularly against colon tumors.

WO 98/09946 in the name of Asta Medica discloses indol-3-glyoxylamide derivatives. The compounds are substituted at the amido nitrogen with aromatic and pyridyl residues and are reported to have antiasthmatic, antiallergic, immunosuppressive and immunomodulating activities.

In *Proceedings of the American Association for Cancer Research*, volume 40, abstract 1893 and 4110, 1999, the compound N-(4-pyridyl)-2-(1-(4-chlorobenzyl)-1H-indol-3-yl)-glyoxylamide (D-24,851) is described to have in vitro and in vivo antitumor effects.

It has now been found that N-(5-oxo-2,5-dihydrofuran-3-yl) or N-(5-oxo-2,5-dihydrothiophen-3-yl)-2-(1H-indol-3-yl)-2-oxo-acetamido derivatives have marked antitumor activity, particularly against human solid tumors.

The compounds of the invention can be represented by the general formula (I):

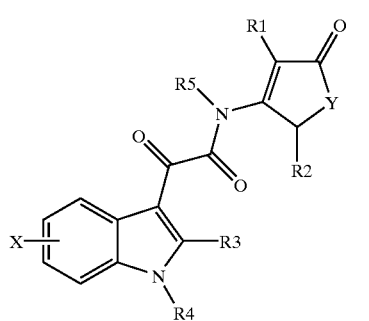

(I)

wherein:
R1, R2 and R5 are independently hydrogen or a C1–C6 alkyl group;
R3 is hydrogen, C1–C4 alkyl, aralkyl, optionally substituted phenyl;
R4 is hydrogen, straight or branched C1–C8 alkyl, C5–C6 cycloalkyl; aralkyl; heteroaralkyl;
X is one or more groups, at most four, independently selected from hydrogen; C1–C6 alkyl; C1–C6 haloalkyl; C1–C6 hydroxyalkyl; C1–C6-aminoalkyl; C1–C6-alkoxy-C1–C6-alkyl; C1–C18-acyloxy-C1–C6-alkyl; hydroxy; C1–C4 alkoxy; C1–C3 haloalkoxy; phenoxy; aralkoxy; C1–C3 acyloxy; amino; C1–C3 alkylamino; C1–C3-acylamino; C1–C3-alkylsulfonylamino; aroylamino; halogen; nitro; cyano; trifluoromethyl; carboxy; C1–C6 alkoxycarbonyl; a RaRbN(CH$_2$)$_n$C(=O)— group wherein Ra and Rb are independently hydrogen, C1–C3-alkyl or Ra and Ro together with the nitrogen atom they are linked to form a pyrrolidino, piperidino, piperazino or morpholino ring and n=0 or an integer from 1 to 4; a RaRcN(CH$_2$)$_n$C(=O)— group wherein Ra and n are as above defined and Rc is a C1–C4-alkoxycarbonyl group; a R1C(=O)— group wherein R1 is as above defined; sulfonyl; mercapto; C1–C4-alkylthio; C1–C4-alkylsulfinyl; C1–C4-alkylsulfonyl; aminosulfonyl; C1–C3-alkylamiosulfonyl; a group —P(=O)(OR1)(OR2) being R1 and R2 as above defined; a group (E)— or (Z)—C(R1)=C(R2)—C(=O)R6 wherein R6 is hydroxy, C1–C6-alkoxy, NRaRb or a group of formula RaRbN(CH$_2$)$_m$NR1—, being m an integer from 2 to 4 and R1, R2, Ra, and Rb as above defined;

Y is an oxygen or sulfur atom, and the isomers, enantiomers and mixtures thereof.

The invention also relates to the salts of compounds of formula (I) obtainable by reacting non toxic acids or bases with the ionisable groups present in compounds (I).

Optionally substituted phenyl preferably means phenyl, 4-methylphenyl, 2,4-dimethoxy-phenyl, 4-methoxy-phenyl, 4-nitro-phenyl, 3-chlorophenyl, 4-hydroxyphenyl, 3,5-dimethoxy-4-hydroxy-phenyl, 3-cyano-phenyl, 2-hydroxyphenyl, 2-carboxyphenyl.

Aralkyl preferably means benzyl, phenethyl, naphthylmethyl, biphenylmethyl, optionally substituted with one or more chloro, fluoro, trifluoromethyl, nitro, cyano, methylsulfonyl, tert-butyl groups.

Heteroaralkyl preferably means pyridylmethyl.

R1 and R2 and R3 and R5 are preferably hydrogen and methyl.

R4 is preferably hydrogen; methyl; benzyl substituted on the benzene ring with one or more groups selected from methyl, t-butyl, fluorine, chlorine, bromine, hydroxy, acetoxy, methoxy, trifluoromethoxy, benzyloxy, trifluoromethyl, cyano, nitro, amino, acetylamino, methylsulfonylamino, methylmercapto, methylsulfinyl, methylsulfonyl, phenyl, ethoxycarbonyl, carboxy, carboxymethyl, (ethoxycarbonyl)methyl, (tert-butoxycarbonyl)methyl, (benzyloxycarbonyl)methyl, (dimethylcarbamoyl)methyl; α-naphthyl, β-naphthyl; 4-pyridyl; 4-pyridyl-N oxide.

X is preferably methyl, ethyl, fluorine, chlorine, bromine, hydroxy, acetoxy, methoxy, phenoxy, trifluoromethoxy, trifluoromethyl, cyano, nitro, amino, acetylamino, methylsulfonylamino, methylmercapto, methylsulfinyl, methylsulfonyl, carboxy, methoxycarbonyl, tert-butoxycarbonyl, diethylcarbamoyl, (2-aminoethyl) carbamoyl, (2-dimethylaminoethyl)carbamoyl, (E)- and (Z)-2-carboxyethen-1-yl, (E)- and (Z)-(2-tert-butoxycarbonyl) ethen-1-yl, (E)- and (Z)—(ethoxycarbonyl)ethenyl, hydroxymethyl, and allyloxymethyl.

Y is preferably an oxygen atom.

The compounds of the invention can be prepared by reacting compounds of formula (II)

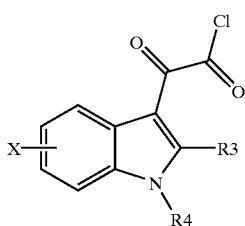

(II)

wherein R3, and R4 and X are as defined above, with a compound of formula (III)

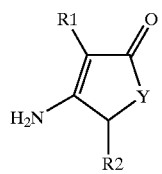

(III)

wherein Y, R1 and R2 are as defined above.

The reaction is carried out in a solvent such as ethyl ether, isopropyl ether, methyl-tert-butyl ether, tetrahydrofuran, dioxane, 1,2-dimethoxyethane, dichloromethane, 1,2-dichloroethane, toluene, dimethylformamide, dimethylacetamide, dimethylsulfoxide, at a temperature ranging from 0° C. to the reflux temperature of the solvent, and using 1 to 3 molar equivalents of compounds of formula (III). Optionally, the reaction can be performed in the presence of the carbonate of an alkaline- or alkaline-earth metal.

The reaction is preferably carried out in an ether solvent such as ethyl ether, THF, or 1,2-dimethoxyethane, at a temperature ranging from room temperature to 80° C., in the presence of at least one equivalent of potassium carbonate.

The resulting compounds of formula (I) can subsequently be transformed into other compounds of formula (I) according to the procedures conventionally used for the transformation of functional groups, for example reactions such as hydrolysis of ester groups, esterification of carboxylic acids, amidation, and the like. For example, when in compounds of formula (II) X and R4 contain substituents which interfere with the reaction of compounds of formula (II) with compounds of formula (III), suitable protective groups will be used and subsequently removed according to conventional methods.

The compounds of formula I in which R5 is a C1–C6 alkyl group are obtained by alkylation of the compounds of formula I in which R5 is hydrogen with a R5-Hal derivative, wherein Hal is preferably chlorine, bromine or iodine, in the presence of the hydride of an alkali- or alkaline-earth metal.

Compounds of formula (II) are obtained by reacting compounds of formula (IV)

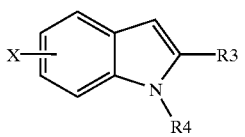

(IV)

wherein X, R3 and R4 are as defined above, with oxalyl chloride.

The reaction is usually carried out in a solvent such as ethyl ether, isopropyl ether, tert-butyl methyl ether, tetrahydrofuran, dioxane, dichloromethane, at a temperature ranging from −10° C. to 25° C. and using from one to two molar equivalents of oxalyl chloride, preferably at 0° C. to 25° C. in ethyl ether or in tetrahydrofuran and using a slight excess (1.2 molar equivalents) of oxalyl chloride. The reaction is usually completed in 3 hours.

Compounds of formula (IV) are obtained by reacting indoles of formula (V)

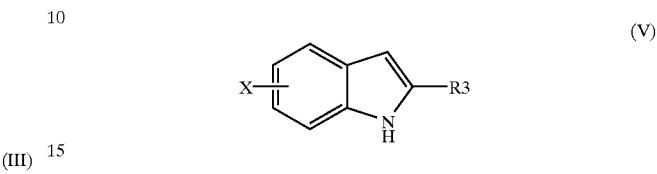

(V)

with halides of formula R4-Hal (VI), wherein Hal is preferably chlorine, bromine or iodine, in the presence of acid-binding agents.

The reaction is usually carried out using an equimolar amount or a slight excess of the halide (VI), in a protic, dipolar aprotic or apolar solvent such as ethanol, isopropanol, tert-butanol, tetrahydrofuran, dioxane, dimethylsulfoxide, dimethylformamide, dimethylacetamide, N-methylpyrrolidinone, acetonitrile, in the presence of an alkali or alkaline-earth metal hydroxide or alkoxide or hydride such as sodium hydroxide, sodium hydride, potassium tert-butoxide. The reaction is carried out at a temperature usually ranging from 0° C. to the reflux temperature of the solvent, for a time from 30' to 24 hours, preferably in dimethylsulfoxide in the presence of sodium hydride in equimolar amount to compounds (V), reacting compounds (V) with sodium hydride at 0°–25° C., then adding compounds (VI) and heating to 50–70° C. The reaction is usually completed in three hours.

Compounds of formulae (V) and (VI) are known or can be prepared by known methods, and many of them are commercially available.

Compounds of formula (III) wherein Y is oxygen are obtained through the reactions described in the following Scheme starting from known compounds of formula (VII). Compounds (VII) are first converted into enamines (VIII) by reaction with an ammonium salt, such as ammonium acetate. Enamines are subsequently converted into compounds (III) in which Y=O by heating in dimethylformamide.

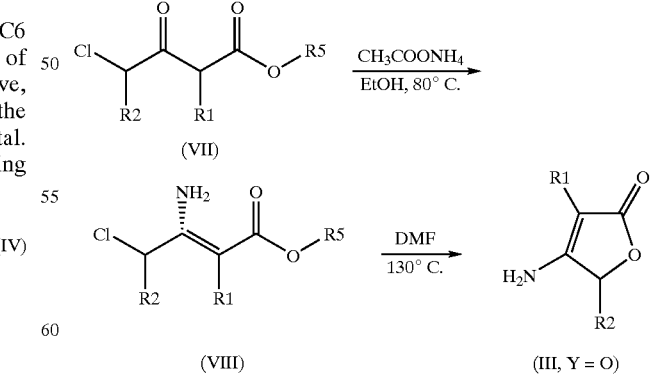

Alternatively, compounds (III) in which Y is oxygen or sulfur can be prepared from the known furanediones or thiophenediones (IX) by melting with an ammonium salt such as ammonium acetate.

The compounds according to the invention have been pharmacologically tested against four human tumor cell lines: HT 29 (colon carcinoma), PC 3 (prostate carcinoma), H 460M (lung carcinoma), MKN-45 (gastric carcinoma). Cells were incubated with the tested compound for 144 hours, then cytotoxicity was determined by using the MTT assay (Mosman, T. "Rapid Colorimetric Assay for Cellular Growth and Survival: Application to Proliferation and Cytotoxicity Assay"; J. Immunolog. Methods, (1983), 65, 66; Green, L. M., "Rapid Colorimetric Assay for Cell Viability; Application to the Quantitation of Cytotoxic and Growth Inhibitory Lymphokines", J. Immunol. Methods, (1984),;70, 257–268).

The obtained data evidenced that the compounds according to the present invention have remarkable activity against solid tumors, in particular colon and lung tumors.

The compounds of the invention can be administered in doses ranging from 0.01 mg to 1 g/kg body weight daily. A preferred dosage regimen may range from about 1 mg to about 500 mg/kg body weight daily, using such unitary doses as to administer in 24 hours from about 70 mg to about 3.5 g of the active substance to a patient weighing about 70 Kg. Such dosage regimen may be adjusted in order to obtain a better therapeutical effect. For example, dosages may be adjusted in consideration of the therapeutical conditions of the patient. The active compounds of the invention can be administered through the oral, intravenous, intramuscular or subcutaneous route.

The compounds of the invention may be administered, according to well-known therapeutical procedures, in combination with other agents used to induce the regression of tumors, in order to synergistically increase the antitumor effects of said compounds. Examples of compounds which can be used in combination with the compounds of the invention are cisplatin, carboplatin, doxorubicin, topotecan, taxol, taxotere, vincristine, 5-fluorouracil.

The pharmaceutical compositions according to the present invention contain therapeutically effective amounts of at least one compound of the invention in mixture with pharmaceutically acceptable excipients.

The oral compositions will generally include an inert diluent or an edible carrier and may be included in gelatin capsules or compressed into tablets. Other forms suitable for oral administration are capsules, pills, elixirs, suspensions or syrups.

The tablets, pills, capsules and similar compositions may contain the following ingredients (in addition to the active substance): a binder such as a microcrystalline cellulose, gum tragacanth or gelatin; an excipient such as starch or lactose; a disintegrating agent such as alginic acid, primogel, corn starch and the like; a lubricant such as magnesium stearate; a glidant such as colloidal silicon dioxide; a sweetening agent such as sucrose or saccharine or a flavoring agent such as peppermint, methyl salicylate or orange flavor. When the chosen composition is in form of capsules, it may contain in addition a liquid carrier such as a fatty oil. Other compositions may contain other various materials which modify the physical form, such as coating agents (for tablets and pills) such as sugar or shellac. The materials used in the preparation of the compositions should be pharmaceutically pure and not toxic at the employed dosages.

For the preparation of pharmaceutical compositions for the parenteral administration, the active ingredient may be incorporated into solutions or suspensions, which may include in addition the following components: a sterile diluent such as water for injection, saline solution, oils, polyethylene glycols, glycerin, propylene glycol or other synthetic solvents; antibacterial agents such as benzyl alcohol; antioxidants such as ascorbic acid or sodium bisulphite; chelating agents such as ethylenediaminotetraacetic acid; buffers such as acetates, citrates or phosphates and agents for adjusting the solution tonicity such as sodium chloride or dextrose. The parenteral preparation may be included in ampoules, disposable syringes or glass or plastic vials.

The invention is further described by the following examples.

Preparation 1: 4-amino-5H-furan-2-one

A solution of ethyl 4-chloroacetoacetate (7.02 ml) and ammonium acetate (11.8 g) in absolute ethanol (180 ml) is refluxed for 3 hours. After a night at room temperature the solution is concentrated to dryness by distillation under reduced pressure and the resulting residue is purified by flash chromatography (silica gel, 200 g; eluent $CH_2Cl_2$/MeOH/TEA 15/5/02), to give 6.53 g of ethyl (Z)-3-amino-4-chloro-2-butenoate as dark oil which is used without further purifications.

1H-NMR (DMSO-d6, ppm): 1.20 (t, 3H); 4.0 (q, 2H); 4.15 (s, 2H); 4.65 (s, 1H); 6.80–7.75 (br. s, 2H).

The Z conformation around the double bond is confirmed by NOE nuclear magnetic resonance tests.

The resulting product (6.30 g) is dissolved in dry dimethylformamide and the solution is heated under nitrogen atmosphere at 100° C. for 2 h.30' and subsequently at 130° C. for 1 h.30'. Dimethylformamide is subsequently distilled off under reduced pressure at 90° C. and the resulting residue is dissolved in absolute ethanol (50 ml) and treated with active charcoal (1.5 g). After filtering off charcoal, the filtrate is concentrated to dryness to give a residue which is purified by flash chromatography (silica gel, 190 g; eluent $CH_2Cl_2$/MeOH 9/1). Chromatographic fractions containing the product are combined, concentrated to dryness and the residue is crystallized from ethyl acetate (3 ml) and isopropyl ether (6 ml), to obtain 2.54 g of 4-amino-5H-furan-2-one.

m.p. 157–159° C.

1H-NMR (DMSO-d6, ppm): 4.45 (s, 1H); 4.57 (s, 2H); 7.20 (br. s, 2H).

Preparation 2: 1-(2,4,6-trimethylbenzyl)indole

A solution of indole (1.185 g) in dry DMSO (3 ml) is dropped into a suspension of sodium hydride (60% mineral oil suspension; 0.44 g) in dry DMSO (10 ml). After two hours, the resulting solution is added with a solution of 2,4,6-trimethylbenzyl chloride (1.9 g) in dry DMSO (2 ml) heating at 60° C. for 6 h. The reaction mixture is kept at room temperature overnight, then poured into water (250 ml) extracted with ethyl acetate and dried ($Na_2SO_4$). The drying agent is filtered off, the solvent is evaporated off under reduced pressure and the resulting residue is purified by column chromatography (silica gel; eluent n-hexane/AcOEt 9/1) to obtain 2.2 g of 1-(2,4,6-trimethylbenzyl)indole.

m.p. 79–81° C.

Preparation 3: 1-(n-octyl)indole

A solution of indole (1.0 g) in dry DMSO (1 ml) is dropped into a suspension of sodium hydride (60% mineral oil suspension; 0.37 g) in dry DMSO (20 ml). The mixture is heated at 60° C. for 1 h. After cooling to room temperature, the resulting solution is added dropwise with a solution of n-octyl bromide (2.82 ml) in dry DMSO (2.8 ml). After a night at room temperature, the reaction mixture is poured into water (200 ml) and extracted with ethyl acetate (2×50 ml). The combined organic phases are washed with a NaCl saturated solution, dried and evaporated to dryness. The resulting residue is purified by column chromatography (silica gel; eluent n-hexane), to obtain 1.86 g of 1-(n-octyl) indole as oil. The compound is characterized through its 1H-NMR spectrum.

Preparation 4: 1-substituted Indoles

Following the procedures described in examples 2 and 3, the following 1-substituted indoles are prepared starting from the suitable indoles and halides, optionally followed by standard chemical transformations of the obtained 1-substituted indoles:

1-(4-chlorobenzyl)-5-chloroindole, oil;
1-(4-chlorobenzyl)-6-chloroindole, oil;
1-(4-chlorobenzyl)-2-methylindole, oil;
1-(4-chlorobenzyl)-5-nitroindole, m.p. 135–137° C.;
1-(4-chlorobenzyl)-6-fluoroindole, oil;
1-[4-(methylsulfonyl)benzyl]-5-chloroindole, m.p. 133–135° C.;
1-(4-chlorobenzyl)-5-methoxyindole, oil;
1-(3-chlorobenzyl)indole, oil;
1-(4-fluorobenzyl)indole, oil;
1-(β-naphthyl)indole, m.p. 106–108° C.;
1-(4-biphenylmethyl)indole, m.p. 130–133° C.;
1-(4-methoxybenzyl)indole, oil;
1-benzylindole, oil;
1-(4-chlorobenzyl)indole, oil;
1-methylindole, oil;
5-chloro-1-(4-chlorobenzyl)-2-methylindole;
5-methoxy-1-(4-chlorobenzyl)-2-methylindole;
1-(4-chlorobenzyl)-2,5-dimethylindole;
4-chloro-1-(4-chlorobenzyl)indole;
4-acetoxy-1-(4-chlorobenzyl)indole;
1-(4-chlorobenzyl)-4-methylindole, oil;
1-(4-chlorobenzyl)-5-cyanoindole, m.p. 108–110° C.;
5-bromo-1-(4-chlorobenzyl)indole, oil;
5,6-dimethoxy-1-(4-chlorobenzyl)indole, oil;
5-benzyloxy-1-(4-chlorobenzyl)indole;
1-(4-chlorobenzyl)-5-(methoxycarbonyl)indole;
5-acetylamino-1-(4-chlorobenzyl)indole;
5-methanesulfonylamino-1-(4-chlorobenzyl)indole;
1-(4-chlorobenzyl)-5-methylindole, oil;
1-(4-chlorobenzyl)-6-methylindole,oil;
1-(4-chlorobenzyl)-7-nitroindole, m.p. 243–245° C.;
1-(4-chlorobenzyl)-7-methylindole,oil;
1-(4-chlorobenzyl)₄-methoxyindole, oil;
1-(4-chlorobenzyl)-4-(ethoxycarbonyl)indole;
1-(4-chlorobenzyl)-4-nitroindole, oil;
4-acetylamino-1-(4-chlorobenzyl)indole;
6-cyano-1-(4-chlorobenzyl)indole;
5,7-dimethoxy-1-(4-chlorobenzyl)indole;
1-(4-chlorobenzyl)-2-phenylindole, oil;
1-(4-chlorobenzyl)-2-phenyl-5-methylindole;
1-(4-chlorobenzyl)-2,7-dimethylindole;
1-(4-chlorobenzyl)-6-methoxyindole;
2-(4-chlorophenyl)-1-ethylindole;
1-(4-chlorobenzyl)-2-(2-pyridyl)indole;
5-benzyloxy-1-(4-chlorobenzyl)-methoxyindole;
7-benzyloxy-1-(4-chlorobenzyl)indole;
1-(4-chlorobenzyl)-5,6-methylenedioxyindole, oil;
1-(4-chlorobenzyl)-2-(4-chlorophenyl)indole;
4-benzyloxy-1-(4-chlorobenzyl)indole;
1-(4-chlorobenzyl)-7-methoxyindole;
1-(4-chlorobenzyl)-4,5,6-trimethoxyindole;
1-(4-chlorobenzyl)-2-ethylindole;
1-(4-chlorobenzyl)-6-nitroindole, oil;
6-benzyloxy-1-(4-chlorobenzyl)indole;
1-(4-chlorobenzyl)-4-fluoroindole, oil;
1-(4-chlorobenzyl)-2-(4-fluorophenyl)indole;
1-(4-chlorobenzyl)-2-(3-chloro-4-fluorophenyl)indole;
1-(4-chlorobenzyl)-2-(3,4-difluorophenyl)indole;
1-(4-chlorobenzyl)-2-methyl-5-nitroindole;
1-(4-chlorobenzyl)-2-(2-naphthyl)indole;
2-(2-acetylaminophenyl)-1-(4-chlorobenzyl)indole;
1-(4-chlorobenzyl)-7-ethylindole;
6-acetoxy-1-(4-chlorobenzyl)indole;
1-(4-chlorobenzyl)-4,7-dimethoxyindole;
1-(4-chlorobenzyl)-4-methoxycarbonylindole, m.p. 62–63° C.;
4-(4-chlorobenzoylamino)-1-(4-chlorobenzyl)indole;
1-(4-chlorobenzyl)-6-methoxycarbonylindole, oil;
1-(4-chlorobenzyl)-7-methoxycarbonylindole;
1-(4-chlorobenzyl)-6-(2-dimethylaminoethylaminocarbonyl)indole;
1-(4-chlorobenzyl)-5-iodoindole;
1-(n-butyl)indole;
1-(4-chlorobenzyl)-4,5,6,7-tetrafluoroindole;
1-(4-chlorobenzyl)-6-trifluoromethylindole;
4-chloro-1-(4-chlorobenzyl)-6-methoxyindole;
6-chloro-1-(4-chlorobenzyl)-4-methoxyindole;
1-(4-chlorobenzyl)-5-phenoxyindole;
1-(4-chlorobenzyl)-2-(2-chlorophenyl)indole;
1-(2-bromobenzyl)indole;
1-(3-bromobenzyl)indole;
1-(4-bromobenzyl)indole, oil;
1-(4-bromobenzyl)6-methylindole;
1-(2-methylbenzyl)indole;
1-(3-methylbenzyl)indole;
1-(4-methylbenzyl)indole, oil;
1-(4-methylbenzyl)-6-fluoroindole;
1-(4-tert-butylbenzyl)indole, oil;
1-(4-tert-butylbenzyl)-6-methoxyindole;
1-(2,3,4,5,6-pentafluorobenzyl)indole, oil;
1-(2-fluorobenzyl)indole, oil;
1-(2,6-difluorobenzyl)indole;
1-(3-fluorobenzyl)indole, oil;
1-(3-fluorobenzyl)-5-bromoindole;
1-(3-trifluoromethylbenzyl)-6-nitroindole;
1-(4-trifluoromethylbenzyl)indole, oil;
1-(4-trifluoromethylbenzyl)-5-methanesulfonylaminoindole;
1-(2-chlorobenzyl)indole, oil;
1-(2,6-dichlorobenzyl)indole;
1-(2-cyanobenzyl)indole;
1-(3-cyanobenzyl)indole, oil;
1-(4-cyanobenzyl)-6-fluoroindole;
1-(4-methoxycarbonylbenzyl)indole;
1-(4-methoxycarbonylbenzyl)-6-fluoroindole;
1-(2-nitrobenzyl)indole;
1-(3-nitrobenzyl)indole, oil;
1-(2-methoxy-5-nitrobenzyl)indole;
1-(4-nitrobenzyl)indole;
1-(3,4-difluorobenzyl)indole, oil;
1-(3,4-difluorobenzyl)-6-methoxyindole;
1-(2,5-difluorobenzyl)indole;
1-(3,5-bis(trifluoromethyl)benzyl)indole;
1-(3,5-difluorobenzyl)indole, oil;

1-(2,4-bis(trifluoromethyl)benzyl)indole;
1-(4-(methoxycarbonylmethyl)benzyl)indole, oil;
1-(2,4-difluorobenzyl)indole;
1-(3,5-dimethylbenzyl)indole;
1-(2-trifluoromethylbenzyl)indole;
1-(2-chloro-6-fluorobenzyl)indole;
1-(3,4-dichlorobenzyl)indole, oil;
1-(3,4-dichlorobenzyl)-6-fluoroindole;
1-(3,4-dichlorobenzyl)-6-methylindole;
1-(2-bromo-5-fluorobenzyl)indole;
1-(2-fluoro-3-methylbenzyl)indole;
1-(2,3-difluorobenzyl)indole;
1-(3-chloro-2-fluorobenzyl)indole;
1-(3-(methoxycarbonyl)benzyl)indole, oil;
1-(3,5-dibromobenzyl)indole;
1-(4-fluoro-2-(trifluoromethyl)benzyl)indole;
1-(2,3,6-trifluorobenzyl)indole, oil;
1-(2,4,5-trifluorobenzyl)indole, oil;
1-(2,4,6-trifluorobenzyl)indole, oil;
1-(2,3,4-trifluorobenzyl)indole, oil;
1-(4-trifluoromethoxybenzyl)indole, oil;
1-(4-trifluoromethoxybenzyl)-6-carbomethoxyindole;
1-(3-trifluoromethoxybenzyl)indole;
1-(2-biphenylmethyl)indole;
1-(4-difluoromethoxybenzyl)indole;
1-(3,4-dimethoxy-6-nitrobenzyl)indole;
1-(3-methoxybenzyl)indole;
1-(2-chloro-4-fluorobenzyl)indole;
1-(2,5-dichlorobenzyl)indole;
1-(4-fluorobenzyl)-4-chloroindole;
1-(4-fluorobenzyl)-5-chloroindole;
1-(4-fluorobenzyl)-6-chloroindole;
1-(4-fluorobenzyl)-2-methylindole;
1-(4-fluorobenzyl)-5-nitroindole;
1-(4-fluorobenzyl)-6-fluoroindole;
1-(4-fluorobenzyl)-5-chloroindole;
1-(4-fluorobenzyl)-5-methoxyindole;
1-(4-fluorobenzyl)-4-methylindole;
1-(4-fluorobenzyl)-5-methylindole;
1-(4-fluorobenzyl)-6-methylindole;
1-(4-fluorobenzyl)-7-methylindole;
1-(4-fluorobenzyl)-5,6-methylenedioxyindole;
1-(3-chlorobenzyl)-5-cyanoindole;
1-(4-biphenylmethyl)-6-carbomethoxyindole;
1-(4-methoxybenzyl)-4-chloroindole;
5-acetylamino-1-benzylindole;
6-fluoro-1-[(4-methylsulfonyl)benzyl]indole;
1-methyl-6-methoxyindole;
5-chloro-1-(methoxybenzyl)-2-methylindole;
1-(4-pyridylmethyl)indole, oil;
1-(4-pyridylmethyl)-6-chloroindole;
1-[4-(methylsulfonyl)benzyl]-1H-indole, m.p. 133–135° C.;
6-bromo-1-(4-chlorobenzyl)-1H-indole, oil;
1-[(3,5-dimethyl-4-isoxazolyl)methyl]-1H-indole, oil;
4-(1H-indol-1-ylmethyl)benzonitrile, oil;
1-(4-chlorobenzyl)-6-phenoxy-1H-indole, oil;
1-(5-chloro-2-fluorobenzyl)-1H-indole, oil;
4(1H-indol-1-ylmethyl)benzoic acid, m.p. 155–158° C.;
4(1H-indol-1-ylmethyl)benzoic acid ethyl ester, oil (prepared by reaction of 4-(1H-indol-1-ylmethyl)benzoic acid with 1,1'-carbonyldiimidazole in THF followed by treatment with absolute ethanol at 70° C. for 3 h);
1-(4-chlorobenzyl)-7-fluoro-1H-indole, oil;
[4-(1H-indol-1-ylmethyl)phenyl]acetic acid;
[4-(1H-indol-1-ylmethyl)phenyl]acetic acid ethyl ester, oil (prepared by reaction of [4-(1H-indol-1-ylmethyl)phenyl]acetic acid with 1,1'-carbonyldiimidazole in THF at room temperature for 4 h, followed by treatment with absolute ethanol at room temperature overnight);
[4(1H-indol-1-ylmethyl)phenyl]acetic acid tert-butyl ester, oil (prepared by reaction of [4-(1H-indol-1-ylmethyl)phenyl]acetic acid with excess N,N-dimethylformamide di-tert-butyl acetal in toluene at 80° C.);
N-[2-(dimethylamino)ethyl]-2-[4(1H-indol-1-ylmethyl)phenyl]acetamide, oil (prepared by reaction of [4-(1H-indol-1-ylmethyl)phenyl]acetic acid with 1,1'-carbonyldiimidazole in THF at room temperature for 3 h followed by treatment with N,N-dimethylethylenediamine at room temperature for 2 h);
3-(1H-indol-1-ylmethyl)benzoic acid methyl ester, oil;
3-(1H-indol-1-ylmethyl)benzoic acid, m.p. 158–160° C. prepared by treatment of an ethanolic solution of 3-(1H-indol-1-ylmethyl)benzoic acid methyl ester with 1N NaOH, followed by acidification with 2N HCl);
N-[2-(dimethylamino)ethyl]-3-(1H-indol-1-ylmethyl)benzamide, oil (prepared by reaction of 3-(1H-indol-1-ylmethyl)benzoic acid with 1,1'-carbonyldiimidazole in THF at room temperature for 2 h followed by treatment with N,N-dimethylethylenediamine at room temperature for 2 h);
[1-(4-chlorobenzyl)-1H-indol-4-yl]methanol, m.p. 66–67° C. (prepared by LiAlH$_4$ reduction of 1-(4-chlorobenzyl)-4-(methoxycarbonyl)-1H-indole);
1-(4-chlorobenzyl)-1H-indole-4-carbaldehyde, m.p. 66–68° C. prepared by oxidation of [1-(4-chlorobenzyl)-1H-indol-4-yl]methanol with excess MnO$_2$ in refluxing CH$_2$Cl$_2$);
1-(4-chlorobenzyl)-1H-indole-4-carboxylic acid, m.p. 190–193° C.;
7-(benzyloxy)-1-(4-fluorobenzyl)-1H-indole, oil;
2-(dimethylamino)ethyl 1-(4-chlorobenzyl)-1H-indole-4-carboxylate, oil (prepared by reaction of 1-(4-chlorobenzyl)-1H-indole-4-carboxylic acid with 1,1'-carbonyldiimidazole in THF at room temperature for 2 h followed by treatment with excess 2-dimethylaminoethanol at reflux temperature);
2-[4-(1H-indol-1-ylmethyl)phenyl]-N,N-dimethylacetamide, oil (prepared by reaction of [4-(1H-indol-1-ylmethyl)phenyl]acetic acid with 1,1'-carbonyldiimidazole in THF at room temperature for 2 h followed by treatment with a 5.2 N solution of dimethylamine in ethanol);
[4-(1H-indol-1-ylmethyl)phenyl]acetic acid benzyl ester, oil (prepared by reaction of [4-(1H-indol-1-ylmethyl)phenyl]acetic acid with 1,1'-carbonyldiimidazole in THF at room temperature for 2 h followed by treatment with benzyl alcohol);
1-(4-chlorobenzyl)-1H-indole-4-carbonitrile, m.p. 85–87° C.;
1-(4-methyl-3-nitrobenzyl)-1H-indole, oil;
(2E)-3-[1-(4-chlorobenzyl)-1H-indol-4-yl]-2-propenoic acid tert-butyl ester, m.p. 91–94° C. (prepared by Wittig reaction of 1-(4-chlorobenzyl)-1H-indole-4-carbaldehyde with Ph$_3$P=CHCOOtBu in refluxing CH$_2$Cl$_2$);
1-(4-chlorobenzyl)-1H-indole-4-carboxylic acid tert-butyl ester, oil (prepared by reaction of 1-(4-chlorobenzyl)-1H-indole-4-carboxylic acid with excess N,N-dimethylformamide di-tert-butyl acetal in toluene at 80° C.);
1-[4(benzyloxy)benzyl]-1H-indole, m.p. 78–80° C.;
1-[1-(4-chlorobenzyl)-1H-indol-4-yl]ethanol (prepared by reaction of 1-(4-chlorobenzyl)-1H-indole-4-carbaldehyde with CH$_3$MgCl in THF at 0° C.);
1-[1-(4-chlorobenzyl)-1H-indol-4-yl]ethanone, m.p. 123–125° C. (prepared by oxidation of 1-[1-(4- chlorobenzyl)-1H-indol-4-yl]ethanol with excess MnO$_2$ in refluxing CHCl$_3$);

2-[4-[(allyloxy)methyl]-1-(4-chlorobenzyl)-1H-indole, oil (prepared by alkylation of [1-(4-chlorobenzyl)-1H-indol-4-yl]methanol with allyl bromide in DMF in the presence of NaH, at room temperature for 3 h).

Preparation 5

4-amino-5H-thiophen-2-one

Commercially available 4-hydroxy-2(5H)-thiophenone (1.16 g) is added to molten ammonium acetate (3.08 g) kept at 130° C. After 30' the molten mixture is cooled and added with 1,2-dimethoxyethane (50 ml). After stirring for 30', the solid is removed by filtration and discarded. The dimethoxyethane solution is concentrated to dryness to give a solid residue which is purified by silica gel column chromatography. Elution is performed initially with CH$_2$Cl$_2$/MeOH 9/1 followed by CH$_2$Cl$_2$/MeOH 8/2. The fastest moving fractions containing the product are pooled and concentrated to dryness, to give 4-amino-5H-thiophen-2-one (0.43 g).

1H-NMR (DMSO-d6, ppm): 3.90 (s, 2H); 4.95 (s, 1H); 7.43 (br. s, 2H).

m.p. 122–260° C.

| Elemental analysis for C$_4$H$_5$NOS: | |
|---|---|
| % calculated: | C = 41.72, H = 4.38, N = 12.16, S = 27.84 |
| % found: | C = 41.81, H = 4.45, N = 11.81, Cl = 27.24. |

EXAMPLE 1

2-(1-(4-chlorobenzyl)-1H-indol-3-yl)-2-oxo-acetyl chloride

A solution of 1-(4-chlorobenzyl)-1H-indole (2.0 g) in dry ethyl ether (5 ml) kept under stirring and cooled to 0° C. is added drop by drop with a solution of oxalyl chloride (0.85 ml) in dry ethyl ether (2 ml). Afterwards the reaction is left at room temperature for 2 h. The separated solid is recovered by filtration, washed with dry ethyl ether and dried under vacuum at 40° C. to give 2-(1-(4-chlorobenzyl)-1H-indol-3-yl)-2-oxo-acetyl chloride (1.64 g).

m.p. 151–153° C.

1H-NMR (CHCl$_3$-d3, ppm): 5.43 (s, 2H); 7.12 (d, 2H); 7.25–7,45 (m, 5H); 8.25 (s, 1H); 8.43 (m, 1H).

EXAMPLE 2

N-(5-oxo-2,5-dihydrofuran-3-yl)-2-(1-(4-chlorobenzyl)-1H-indol-3-yl)-2-oxo-acetamide A solution of 2-(1-(4-chlorobenzyl)-1H-indol-3-yl)-2-oxo-acetyl chloride (0.45 g) and 4-amino-5H-furan-2-one (0.30 g) in dry tetrahydrofuran (10 ml) is refluxed for 2 h. After cooling at room temperature, the reaction mixture is poured into water (200 ml) and the resulting suspension is left under stirring for 1 h. The solid is filtered off and resuspended in methanol (4.3 ml) under stirring for 1 h, then collected by filtration to give N-(5-oxo-2,5-dihydrofuran-3-yl)-2-(1-(4-chlorobenzyl)-1H-indol-3-yl)-2-oxo-acetamide (0.27 g).

m.p. 253–255° C.

1H-NMR (DMSO-d6, ppm): 5.13 (s, 2H); 5.65 (s, 2H); 6.05 (s, 1H); 7.25–7.50 (m, 6H); 7.65 (m, 1H); 8.30 (m, 1H); 9.05 (s, 1H); 11.90 (s, 1H).

| Elemental analysis: | |
|---|---|
| % calculated for C$_{21}$H$_{15}$ClN$_3$O$_4$: | C = 63.89, H = 3.83, N = 7.10. Cl = 8.98 |
| % found: | C = 63.65, H = 4.02, N = 6.89, Cl = 9.13 |

EXAMPLE 3

N-(5-oxo-2,5-dihydrofuran-3-yl)-2-(1-(4-fluorobenzyl)-1H-indol-3-yl)-2-oxo-acetamide A solution of 1-(4-fluorobenzyl)-1H-indole (0.50 g) in dry ethyl ether (5 ml) is added drop by drop with a stirred solution of oxalyl chloride (0.209 ml) in dry ethyl ether (5 ml) cooled at 0° C. Afterwards, the reaction mixture is left at room temperature for 2 h, then is evaporated to dryness, the resulting residue is redissolved in dry tetrahydrofuran (5 ml) and the solution is added drop by drop to a solution of 4-amino-5H-furan-2-one (0.45 g) in dry tetrahydrofuran (22 ml). After that, the mixture is refluxed for 3 h. After a night at room temperature, the reaction mixture is poured into water (300 ml) and the resulting suspension is stirred for 1 h. The solid is collected by filtration and resuspended in hot methanol (20 ml) under stirring for 30'. After 2 h at room temperature, the solid is recovered by filtration to give N-(5-oxo-2,5-dihydrofuran-3-yl)-2-(1-(4-fluorobenzyl)-1H-indol-3-yl)-2-oxo-acetamide (0.35 g).

m.p. 260–262° C.

1H-NMR (DMSO-d6, ppm): 5.15 (s, 2H); 5.65 (s, 2H); 6.05 (s, 1H); 7.10–7.25 (m, 1H); 7.25–7.50 (2m, 4+1H); 7.65 (m, 1H); 8.30 (m, 1H); 9.1 (s, 1H); 11.90 (s, 1H).

| Elemental analysis: | |
|---|---|
| % calculated for C$_{21}$H$_{15}$FN$_2$O$_4$: | C = 66.66, H = 4.00. N = 7.40. F = 5.02 |
| % found: | C = 66.43, H = 4.12, N = 7.18, F = 4.96 |

EXAMPLE 4

Following procedures similar to those described in examples 1–3 and using the suitable 1-substituted indoles as starting products, the following compounds are prepared:

N-(5-oxo-2,5-dihydrofuran-3-yl)-2-(5-chloro-1-(4-chlorobenzyl)-1H-indol-3-yl)-2-oxo-acetamide;

m.p. 251–253° C. (from AcOEt/Et2O);

1H-NMR (DMSO-d6, ppm): 5.13 (s, 2H); 5.65 (s, 2H); 6.05 (s, 1H); 7.40 (m, 5H); 7.65 (d, 1H); 8.23 (s, 1H); 9.12 (s, 1H); 11.87 (s, 1H).

| Elemental analysis for C21H14ClN2O4: | |
|---|---|
| % calculated: | C = 58.76, H = 3.29, N = 6.53, Cl = 16.52 |
| % found: | C = 58.11, H = 3.43, N = 6.40, Cl = 15.58 |

N-(5-oxo-2,5-dihydrofuran-3-yl)-2-(6-chloro 1-(4-chlorobenzyl)-1H-indol-3-yl)-2-oxo-acetamide;

m.p. 255–257° C. (from AcOEt/Et2O);

1H-NMR (DMSO-d6, ppm): 5.13 (s, 2H); 5.68 (s, 2H); 6.05 (s, 1H); 7.35 (m, 5H); 7.80 (s, 1H); 8.23 (d, 1H); 9.10 (s, 1H); 11.87 (s, 1H).

Elemental analysis for $C_{21}H_{14}ClN_2O_4$:

| | |
|---|---|
| % calculated: | C = 58.76, H = 3.29, N = 6.53, Cl = 16.52 |
| % found: | C = 58.08 H = 3.39, N = 6.10, Cl = 15.71 |

N-(5-oxo-2,5-dihydrofuran-3-yl)-2-(1-(4-chlorobenzyl)-2-methyl-1H-indol-3-yl)-2-oxo-acetamide;

m.p. 254–256° C. (from isopropyl alcohol);

1H-NMR (DMSO-d6, ppm): 2.65 (s, 3H); 5.15 (s, 2H); 5.65 (s, 2H); 5.95 (s, 1H); 7.07 (d, 2H); 7.23 (m, 4H); 7.40 (d, 2H); 7.63 (m, 1H); 7.93 (m, 1H); 11.98 (s, 1H).

Elemental analysis for $C_{22}H_{17}ClN_2O_4$:

| | |
|---|---|
| % calculated: | C = 64.63, H = 4.19, N = 6.85, Cl = 8.67 |
| % found: | C = 64.39, H = 4.23, N = 6.80, Cl = 8.62 |

N-(5-oxo-2,5-dihydrofuran-3-yl)-2-(1-(4-chlorobenzyl)-5-nitro-1H-indol-3-yl)-2-oxo-acetamide;

m.p. 248–250° C. (from MeOH);

Elemental analysis for $C_{21}H_{14}ClN_3O_6$:

| | |
|---|---|
| % calculated: | C = 57.35, H = 3.21, N = 9.55 |
| % found: | C = 56.55, H = 3.16, N = 9.05 |

N-(5-oxo-2,5-dihydrofuran-3-yl)-2-(1-(4-chlorobenzyl)-6-fluoro-1H-indol-3-yl)-2-oxo-acetamide;

m.p. 242–245° C. (from methanol);

Elemental analysis for $C_{21}H_{14}ClFN_2O_4$:

| | |
|---|---|
| % calculated: | C = 61.10, H = 3.42, N = 6.79, Cl = 8.59, F = 4.60 |
| % found: | C = 61.09, H = 3.43, N = 6.76, Cl = 8.55, F = 4.60 |

N-(5-oxo-2,5-dihydrofuran-3-yl)-2-(1-(4-methylsulfonyl)benzyl)-1H-indol-3-yl)-2-oxo-acetamide;

m.p. 283–285° C. (from methanol and AcOEt);

Elemental analysis for $C_{22}H_{18}N_2O_6S$:

| | |
|---|---|
| % calculated: | C = 60.27, H = 4.14, N = 6.39, S = 7.31 |
| % found: | C = 59.07, H = 4.21, N = 6.25, S = 6.42 |

N-(5-oxo-2,5-dihydrofuran-3-yl)-2-(1-(4-chlorobenzyl)-5-methoxy-1H-indol-3-yl)-2-oxo-acetamide;

m.p. 238–240° C. (from MeOH and AcOEt);

1H-NMR (DMSO-d6, ppm): 3.80 (s, 3H); 5.13 (s, 2H); 5.65 (s, 2H); 6.05 (s, 1H); 6.95 (m, 1H); 7.30–7.55 (m, 5H); 7.80 (m, 1H); 9.00 (s, 1H); 11.90 (s, 1H).

Elemental analysis for $C_{22}H_{17}ClN_2O_5$:

| | |
|---|---|
| % calculated: | C = 62.20, H = 4.03, N = 6.59, Cl = 8.34 |
| % found: | C = 62.00. H = 4.01, N = 6.52, Cl = 8.81 |

N-(5-oxo-2,5-dihydrofuran-3-yl)-2-(1-(3-chlorobenzyl)-1H-indol-3-yl)-2-oxo-acetamide;

m.p. 268–270° C. (from MeOH);

Elemental analysis for $C_{21}H_{15}ClN_2O_4$:

| | |
|---|---|
| % calculated: | C = 63.89, H = 3.83, N = 7.10, Cl = 8.98 |
| % found: | C = 64.83, H = 3.98, N = 6.90, Cl = 8.63 |

N-(5-oxo-2,5-dihydrofuran-3-yl)-2-(1-(2-naphthylmethyl)-1H-indol-3-yl)-2-oxo-acetamide;

m.p. 283–285° C. (from AcOEt);

1H-NMR (DMSO-d6, ppm): 5.15 (s, 2H); 5.80 (s, 2H); 6.05 (s, 1H); 7.10–7.25 (m, 2H); 7.25–7.50 (m, 2H); 7.65 (m, 1H); 7.90 (m, 5H); 8.30 (m, 1H); 9.10 (s, 1 H); 11.90 (s, 1H).

N-(5-oxo-2,5-dihydrofuran-3-yl)-2-(1-(4-methoxybenzyl)-1H-indol-3-yl)-2-oxo-acetamide;

m.p. 265–267° C. (from methanol);

1H-NMR (DMSO-d6, ppm): 5.15 (s, 2H); 5.60 (s, 2H); 6.05 (s, 1H); 6.90 (d, 2H); 7.35 (2m, 4H); 7.65 (m, 11H); 8.30 (m, 1H); 9.05 (s, 1H); 11.90 (s, 1H).

Elemental analysis for $C_{22}H_{18}N_2O_5$:

| | |
|---|---|
| % calculated: | C = 67.69, H = 4.65, N = 7.18 |
| % found: | C = 66.78, H = 4.67, N = 6.84 |

N-(5-oxo-2,5-dihydrofuran-3-yl)-2-(1-(2,4,6-trimethylbenzyl)-1H-indol-3-yl)-2-oxo-acetamide;

m.p. 288–290° C. (from AcOEt);

1H-NMR (DMSO-d6, ppm): 2.40 (s, 6H); 2.40 (s, 6H); 5.05 (s, 2H); 5.45 (s, 2H); 5.95 (s, 1H); 7.00 (s, 2H); 7.40 (m, 2H); 7.80 (m, 1H); 8.25 (s, 1H); 8.35 (m, 1H); 11.85 (s, 1H).

Elemental analysis for $C_{24}H_{22}N_2O_4$:

| | |
|---|---|
| % calculated: | C = 71.63, H = 5.51, N = 6.96 |
| % found: | C = 70.70, H = 5.53, N = 6.69 |

N-(5-oxo-2,5-dihydrofuran-3-yl)-2-(1-benzyl-1H-indol-3-yl)-2-oxo-acetamide;

m.p. 275–277° C. (from methanol);

1H-NM (DMSO-d6, ppm): 5.10 (s, 2H); 5.85 (s, 2H); 6.05 (s, 1H); 7.30 (m, 7H); 7.60 (m, 1H); 8.25 (m, 1H); 9.05 (S, 1H); 11.90 (s, 1H).

| Elemental analysis for $C_{21}H_{16}N_2O_4$: | |
|---|---|
| % calculated: | C = 69.99, H = 4.48, N = 7.77 |
| % found: | C = 69.36, H = 4.59, N = 7.45 |

N-(5-oxo-2,5-dihydrofuran-3-yl)-2-(1-(4-biphenylmethyl)-1H-indol-3-yl)-2-oxo-acetamide m.p. 245–248° C.

1H-NMR (DMSO-d6, ppm): 5.10 (s, 2H); 5.85 (s, 2H); 6.05 (s, 1H); 7.35 (m, 7H); 7.70 (m, 5H); 8.25 (m, 1H); 9.05 (s, 1H); 11.87 (s, 1H).

N-(5-oxo-2,5-dihydrofuran-3-yl)-2(1-(n-octyl)-1H-indol-3-yl)-2-oxo-acetamide;

m.p. 224–226° C. (from methanol);

1H-NMR (DMSO-d6, ppm): 0.80 (t, 3H); 1.05–1.40 (m, 10H); 4.40 (t, 2H); 5.13 (s, 2H); 6.05 (s, 1H); 7.35 (m, 2H); 7.67 (m, 1H); 8.30 (m, 1H); 8.85 (s, 1H); 11.90 (s, 1H).

N-(5-oxo-2,5-dihydrofuran-3-yl)-2-(1-methyl-1H-indol-3-yl)-2-oxo-acetamide;

m.p. 262–264° C. (from methanol);

1H-NMR (DMSO-d6, ppm): 3.95 (s, 3H); 5.15 (s, 2H); 6.03 (s, 1H); 7.35 (m, 2H); 7.65 (m, 1H); 8.30 (m, 1H); 8.85 (s, 1H); 11.90 (s, 1H).

N-(5-oxo-2,5-dihydrofuran-3-yl)-2-(5-chloro-1-(4-chlorobenzyl)-2-methyl-1H-indol-3-yl)-2-oxo-acetamide;

N-(5-oxo-2,5-dihydrofuran-3-yl)-2-(5-methoxy-1-(4-chlorobenzyl)-2-methyl-1H-indol-3-yl)-2-oxo-acetamide;

N-(5-oxo-2,5-dihydrofuran-3-yl)-2-(1-(4-chlorobenzyl)-2,5-dimethyl-1H-indol-3-yl)-2-oxo-acetamide;

N-(5-oxo-2,5-dihydrofuran-3-yl)-2-(4-chloro-1-(4-chlorobenzyl)-1H-indol-3-yl)-2-oxo-acetamide;

N-(5-oxo-2,5-dihydrofuran-3-yl)-2-(4-acetoxy-1-(4-chlorobenzyl)-1H-indol-3-yl)-2-oxo-acetamide;

N-(5-oxo-2,5-dihydrofuran-3-yl)-2-(1-(4-chlorobenzyl)-4-methyl-1H-indol-3-yl)-2-oxo-acetamide, m.p. 217–219°C.;

N-(5-oxo-2,5-dihydrofuran-3-yl)-2-(1-(4-chlorobenzyl)-5-cyano-1H-indol-3-yl)-2-oxo-acetamide, m.p. 284–287°C.;

N-(5-oxo-2,5-dihydrofuran-3-yl)-2-(5-bromo-1-(4-chlorobenzyl)-1H-indol-3-yl)-2-oxo-acetamide, m.p. 283–285°C.;

N-(5-oxo-2,5-dihydrofuran-3-yl)-2-(5,6-dimethoxy-1-(4-chlorobenzyl)-1H-indol-3-yl)-2-oxo-acetamide, m.p. 275–277°C.;

N-(5-oxo-2,5-dihydrofuran-3-yl)-2-(5-benzyloxy-1-(4-chlorobenzyl)-1H-indol-3-yl)-2-oxo-acetamide;

N-(5-oxo-2,5-dihydrofuran-3-yl)-2-(1-(4-chlorobenzyl)-5-(methoxycarbonyl)-1H-indol-3-yl)-2-oxo-acetamide;

N-(5-oxo-2,5-dihydrofuran-3-yl)-2-(5-acetylamino-1-(4-chlorobenzyl)-1H-indol-3-yl)-2-oxo-acetamide;

N-(5-oxo-2,5-dihydrofuran-3-yl)-2-(5-methanesulfonylamino-1-(4-chlorobenzyl)-1H-indol-3-yl)-2-oxo-acetamide;

N-(5-oxo-2,5-dihydrofuran-3-yl)-2-(1-(4-chlorobenzyl)-5-methyl-1H-indol-3-yl)-2-oxo-acetamide, m.p. 277–280°C.

N-(5-oxo-2,5-dihydrofuran-3-yl)-2-(1-(4-chlorobenzyl)-6-methyl-1H-indol-3-yl)-2-oxo-acetamide, m.p. 282–284° C.;

N-(5-oxo-2,5-dihydrofuran-3-yl)-2-(1-(4-chlorobenzyl)-7-nitro-1H-indol-3-yl)-2-oxo-acetamide, m.p. 243–245°C.;

N-(5-oxo-2,5-dihydrofuran-3-yl)-2-(1-(4-chlorobenzyl)-7-methyl-1H-indol-3-yl)-2-oxo-acetamide, m.p. 268–270° C.;

N-(5-oxo-2,5-dihydrofuran-3-yl)-2-(1-(4-chlorobenzyl)-4-methoxy-1H-indol-3-yl)-2-oxo-acetamide, m.p. 210–212° C.;

N-(5-oxo-2,5-dihydrofuran-3-yl)-2-(1-(4-chlorobenzyl)-4-(ethoxycarbonyl)-1H-indol-3-yl)-2-oxo-acetamide;

N-(5-oxo-2,5-dihydrofuran-3-yl)-2-(1-(4-chlorobenzyl)-4-nitro-1H-indol-3-yl)-2-oxo-acetamide, m.p. 242–244°C.;

N-(5-oxo-2,5-dihydrofuran-3-yl)-2-(4-acetylamino-1-(4-chlorobenzyl)-1H-indol-3-yl)-2-oxo-acetamide;

N-(5-oxo-2,5-dihydrofuran-3-yl)-2-(6-cyano-1-(4-chlorobenzyl)-1H-indol-3-yl)-2-oxo-acetamide;

N-(5-oxo-2,5-dihydrofuran-3-yl)-2-(5,7-dimethoxy-1-(4-chlorobenzyl)-1H-indol-3-yl)-2-oxo-acetamide;

N-(5-oxo-2,5-dihydrofuran-3-yl)-2-(1-(4-chlorobenzyl)-2-phenyl-1H-indol-3-yl)-2-oxo-acetamide, m.p. 280–282°C.;

N-(5-oxo-2,5-dihydrofuran-3-yl)-2-(1-(4-chlorobenzyl)-2-phenyl-5-methyl-1H-indol-3-yl)-2-oxo-acetamide;

N-(5-oxo-2,5-dihydrofuran-3-yl)-2-(1-(4-chlorobenzyl)-2,7-dimethyl-1H-indol-3-yl)-2-oxo-acetamide;

N-(5-oxo-2,5-dihydrofuran-3-yl)-2-(1-(4-chlorobenzyl)-6-methoxy-1H-indol-3-yl)-2-oxo-acetamide, m.p. 283–285°C.;

N-(5-oxo-2,5-dihydrofuran-3-yl)-2-(2-(4-chlorophenyl)-1-ethyl-1H-indol-3-yl)-2-oxo-acetamide;

N-(5-oxo-2,5-dihydrofuran-3-yl)-2-(1-(4-chlorobenzyl)-2-(2-pyridyl)-1H-indol-3-yl)-2-oxo-acetamide;

N-(5-oxo-2,5-dihydrofuran-3-yl)-2-(5-benzyloxy-1-(4-chlorobenzyl)-6-methoxy-1H-indol-3-yl)-2-oxo-acetamide;

N-(5-oxo-2,5-dihydrofuran-3-yl)-2-(7-benzyloxy-1-(4-chlorobenzyl)-1H-indol-3-yl)-2-oxo-acetamide, m.p. 277–280°C.;

N-(5-oxo-2,5-dihydrofuran-3-yl)-2-(1-(4-chlorobenzyl)-5,6-methylenedioxy-1H-indol-3-yl)-2-oxo-acetamide, m.p. 296–298°C.;

N-(5-oxo-2,5-dihydrofuran-3-yl)-2-(1-(4-chlorobenzyl)-2-(4-chlorophenyl)-1H-indol-3-yl)-2-oxo-acetamide;

N-(5-oxo-2,5-dihydrofuran-3-yl)-2-(4-benzyloxy-1-(4-chlorobenzyl)-1H-indol-3-yl)-2-oxo-acetamide;

N-(5-oxo-2,5-dihydrofuran-3-yl)-2-(1-(4-chlorobenzyl)-7-methoxy-1H-indol-3-yl)-2-oxo-acetamide;

N-(5-oxo-2,5-dihydrofuran-3-yl)-2-(1-(4-chlorobenzyl)-4,5,6-trimethoxy-1H-indol-3-yl)-2-oxo-acetamide;

N-(5-oxo-2,5-dihydrofuran-3-yl)-2-(1-(4-chlorobenzyl)-2-ethyl-1H-indol-3-yl)-2-oxo-acetamide;

N-(5-oxo-2,5-dihydrofuran-3-yl)-2-(1-(4-chlorobenzyl)-6-nitro-1H-indol-3-yl)-2-oxo-acetamide, m.p. 192–195°C.;

N-(5-oxo-2,5-dihydrofuran-3-yl)-2-(6-benzyloxy-1-(4-chlorobenzyl)-1H-indol-3-yl)-2-oxo-acetamide;

N-(5-oxo-2,5-dihydrofuran-3-yl)-2-(4-fluoro-1-(4-chlorobenzyl)-1H-indol-3-yl)-2-oxo-acetamide, m.p. 182–185°C.;

N-(5-oxo-2,5-dihydrofuran-3-yl)-2-(6-fluoro-1-(4-chlorobenzyl)-1H-indol-3-yl)-2-oxo-acetamide, m.p. 242–245° C.;

N-(5-oxo-2,5-dihydrofuran-3-yl)-2-(1-(4-chlorobenzyl)-2-(4-fluorophenyl)-1H-indol-3-yl)-2-oxo-acetamide;

N-(5-oxo-2,5-dihydrofuran-3-yl)-2-(1-(4-chlorobenzyl)-2-(3-chloro-4-fluorophenyl)-1H-indol-3-yl)-2-oxo-acetamide;

N-(5-oxo-2,5-dihydrofuran-3-yl)-2-(1-(4-chlorobenzyl)-2-(3,4-difluorophenyl)-1H-indol-3-yl)-2-oxo-acetamide;

N-(5-oxo-2,5-dihydrofuran-3-yl)-2-(5-acetylamino-1-(4-chlorobenzyl)-1H-indol-3-yl)-2-oxo-acetamide;

N-(5-oxo-2,5-dihydrofuran-3-yl)-2-(1-(4-chlorobenzyl)-2-methyl-5-nitro-1H-indol-3-yl)-2-oxo-acetamide;

N-(5-oxo-2,5-dihydrofuran-3-yl)-2-(1-(4-chlorobenzyl)-2-(2-naphthyl)-1H-indol-3-yl)-2-oxo-acetamide;

N-(5-oxo-2,5-dihydrofuran-3-yl)-2-(2-(2-acetylaminophenyl)-1-(4-chlorobenzyl)-1H-indol-3-yl)-2-oxo-acetamide;

N-(5-oxo-2,5-dihydrofuran-3-yl)-2-(1-(4-chlorobenzyl)-7-ethyl-1H-indol-3-yl)-2-oxo-acetamide;

N-(5-oxo-2,5-dihydrofuran-3-yl)-2-(6-acetoxy-1-(4-chlorobenzyl)-1H-indol-3-yl)-2-oxo-acetamide;

N-(5-oxo-2,5-dihydrofuran-3-yl)-2-(1-(4-chlorobenzyl)-4,7-dimethoxy-1H-indol-3-yl)-2-oxo-acetamide;

N-(5-oxo-2,5-dihydrofuran-3-yl)-2-(1-(4-chlorobenzyl)-4-methoxycarbonyl-1H-indol-3-yl)-2-oxo-acetamide, m.p. 212–215° C.;

N-(5-oxo-2,5-dihydrofuran-3-yl)-2-(4-(4-chlorobenzoylamino)-1-(4-chlorobenzyl)-1H-indol-3-yl)-2-oxo-acetamide;

N-(5-oxo-2,5-dihydrofuran-3-yl)-2-(1-(4-chlorobenzyl)-6-methoxycarbonyl-1H-indol-3-yl)-2-oxo-acetamide, m.p. >300° C.;

N-(5-oxo-2,5-dihydrofuran-3-yl)-2-(1-(4-chlorobenzyl)-7-methoxycarbonyl-1H-indol-3-yl)-2-oxo-acetamide;

N-(5-oxo-2,5-dihydrofuran-3-yl)-2-(1-(4-chlorobenzyl)-6-(2-dimethylamino-ethylaminocarbonyl)-1H-indol-3-yl)-2-oxo-acetamide;

N-(5-oxo-2,5-dihydrofuran-3-yl)-2-(1-(4-chlorobenzyl)-5-iodo-1H-indol-3-yl)-2-oxo-acetamide;

N-(5-oxo-2,5-dihydrofuran-3-yl)-2-(1-(n-butyl)-1H-indol-3-yl)-2-oxo-acetamide;

N-(5-oxo-2,5-dihydrofuran-3-yl)-2-(1-(4-chlorobenzyl)-4,5,6,7-tetrafluoro-1H-indol-3-yl)-2-oxo-acetamide;

N-(5-oxo-2,5-dihydrofuran-3-yl)-2-(1-(4-chlorobenzyl)-6-trifluoromethyl-1H-indol-3-yl)-2-oxo-acetamide;

N-(5-oxo-2,5-dihydrofuran-3-yl)-2-(4-chloro-1-(4-chlorobenzyl)-6-methoxy-1H-indol-3-yl)-2-oxo-acetamide;

N-(5-oxo-2,5-dihydrofuran-3-yl)-2-(6-chloro-1-(4-chlorobenzyl)-4-methoxy-1H-indol-3-yl)-2-oxo-acetamide;

N-(5-oxo-2,5-dihydrofuran-3-yl)-2-(1-(4-chlorobenzyl)-5-phenoxy-1H-indol-3-yl)-2-oxo-acetamide;

N-(5-oxo-2,5-dihydrofuran-3-yl)-2-(1-(2-bromobenzyl)-1H-indol-3-yl)-2-oxo-acetamide;

N-(5-oxo-2,5-dihydrofuran-3-yl)-2-(1-(3-bromobenzyl)-1H-indol-3-yl)-2-oxo-acetamide;

N-(5-oxo-2,5-dihydrofuran-3-yl)-2-(1-(4-bromobenzyl)-1H-indol-3-yl)-2-oxo-acetamide, m.p. 278–280° C.;

N-(5-oxo-2,5-dihydrofuran-3-yl)-2-(1-(4-bromobenzyl)-6-methyl-1H-indol-3-yl)-2-oxo-acetamide;

N-(5-oxo-2,5-dihydrofuran-3-yl)-2-(1-(2-methylbenzyl)-1H-indol-3-yl)-2-oxo-acetamide;

N-(5-oxo-2,5-dihydrofuran-3-yl)-2-(1-(3-methylbenzyl)-1H-indol-3-yl)-2-oxo-acetamide;

N-(5-oxo-2,5-dihydrofuran-3-yl)-2-(1-(4-methylbenzyl)-1H-indol-3-yl)-2-oxo-acetamide, m.p. 298–300° C.;

N-(5-oxo-2,5-dihydrofuran-3-yl)-2-(1-(4-methylbenzyl)-6-fluoro-1H-indol-3-yl)-2-oxo-acetamide;

N-(5-oxo-2,5-dihydrofuran-3-yl)-2-(1-(4-tert-butylbenzyl)-1H-indol-3-yl)-2-oxo-acetamide, m.p. 218–220° C.;

N-(5-oxo-2,5-dihydrofuran-3-yl)-2-(1-(4-tert-butylbenzyl)-6-methoxy-1H-indol-3-yl)-2-oxo-acetamide;

N-(5-oxo-2,5-dihydrofuran-3-yl)-2-(1-(2,3,4,5,6-pentafluorobenzyl)-1H-indol-3-yl)-2-oxo-acetamide;

N-(5-oxo-2,5-dihydrofuran-3-yl)-2-(1-(2-fluorobenzyl)-1H-indol-3-yl)-2-oxo-acetamide, m.p. 280–282° C.;

N-(5-oxo-2,5-dihydrofuran-3-yl)-2-(1-(2,6-difluorobenzyl)-1H-indol-3-yl)-2-oxo-acetamide;

N-(5-oxo-2,5-dihydrofuran-3-yl)-2-(1-(3-fluorobenzyl)-1H-indol-3-yl)-2-oxo-acetamide, m.p. 252–256° C.;

N-(5-oxo-2,5-dihydrofuran-3-yl)-2-(1-(3-fluorobenzyl)-5-bromo-1H-indol-3-yl)-2-oxo-acetamide;

N-(5-oxo-2,5-dihydrofuran-3-yl)-2-(1-(3-trifluoromethylbenzyl)-6-nitro-1H-indol-3-yl)-2-oxo-acetamide;

N-(5-oxo-2,5-dihydrofuran-3-yl)-2-(1-(4-trifluoromethylbenzyl)-1H-indol-3-yl)-2-oxo-acetamide, m.p. 279–281° C.;

N-(5-oxo-2,5-dihydrofuran-3-yl)-2-(1-(4-trifluoromethylbenzyl)-5-(methanesul-fonylamino)-1H-indol-3-yl)-2-oxo-acetamide;

N-(5-oxo-2,5-dihydrofuran-3-yl)-2-(1-(2-chlorobenzyl)-1H-indol-3-yl)-2-oxo-acetamide, m.p. 267–269° C.;

N-(5-oxo-2,5-dihydrofuran-3-yl)-2-(1-(2,6-dichlorobenzyl)-1H-indol-3-yl)-2-oxo-acetamide;

N-(5-oxo-2,5-dihydrofuran-3-yl)-2-(1-(2-cyanobenzyl)-1H-indol-3-yl)-2-oxo-acetamide;

N-(5-oxo-2,5-dihydrofuran-3-yl)-2-(1-(3-cyanobenzyl)-1H-indol-3-yl)-2-oxo-acetamide, m.p. 229–231° C.;

N-(5-oxo-2,5-dihydrofuran-3-yl)-2-(1-(4-cyanobenzyl)-6-fluoro-1H-indol-3-yl)-2-oxo-acetamide;

N-(5-oxo-2,5-dihydrofuran-3-yl)-2-(1-(4-methoxycarbonylbenzyl)-1H-indol-3-yl)-2-oxo-acetamide;

N-(5-oxo-2,5-dihydrofuran-3-yl)-2-(1-(4-methoxycarbonylbenzyl)-6-fluoro-1H-indol-3-yl)-2-oxo-acetamide;

N-(5-oxo-2,5-dihydrofuran-3-yl)-2-(1-(2-nitrobenzyl)-1H-indol-3-yl)-2-oxo-acetamide;

N-(5-oxo-2,5-dihydrofuran-3-yl)-2-(1-(3-nitrobenzyl)-1H-indol-3-yl)-2-oxo-acetamide, m.p. 257–260° C.;

N-(5-oxo-2,5-dihydrofuran-3-yl)-2-(1-(2-methoxy-5-nitrobenzyl)-1H-indol-3-yl)-2-oxo-acetamide;

N-(5-oxo-2,5-dihydrofuran-3-yl)-2-(1-(4-nitrobenzyl)-1H-indol-3-yl)-2-oxo-acetamide;

N-(5-oxo-2,5-dihydrofuran-3-yl)-2-(1-(3,4-difluorobenzyl)-1H-indol-3-yl)-2-oxo-acetamide, m.p. 275–277° C.;

N-(5-oxo-2,5-dihydrofuran-3-yl)-2-(1-(3,4-difluorobenzyl)-6-methoxy-1H-indol-3-yl)-2-oxo-acetamide;

N-(5-oxo-2,5-dihydrofuran-3-yl)-2-(1-(2,5-difluorobenzyl)-1H-indol-3-yl)-2-oxo-acetamide;

N-(5-oxo-2,5-dihydrofuran-3-yl)-2-(1-(3,5-bis(trifluoromethyl)benzyl)-1H-indol-3-yl)-2-oxo-acetamide;

N-(5-oxo-2,5-dihydrofuran-3-yl)-2-(1-(3,5-difluorobenzyl)-1H-indol-3-yl)-2-oxo-acetamide, m.p. 276–278° C.;

N-(5-oxo-2,5-dihydrofuran-3-yl)-2-(1-(2,4-bis(trifluoromethyl)benzyl)-1H-indol-3-yl)-2-oxo-acetamide;

N-(5-oxo-2,5-dihydrofuran-3-yl)-2-(1-(4-(methoxycarbonylmethyl)benzyl)-1H-indol-3-yl)-2-oxo-acetamide;

N-(5-oxo-2,5-dihydrofuran-3-yl)-2-(1-(2,4-difluorobenzyl)-1H-indol-3-yl)-2-oxo-acetamide;

N-(5-oxo-2,5-dihydrofuran-3-yl)-2-(1-(3,5-dimethylbenzyl)-1H-indol-3-yl)-2-oxo-acetamide;

N-(5-oxo-2,5-dihydrofuran-3-yl)-2-(1-(2-trifluoromethylbenzyl)-1H-indol-3-yl)-2-oxo-acetamide;

N-(5-oxo-2,5-dihydrofuran-3-yl)-2-(1-(2-chloro-6-fluorobenzyl)-1H-indol-3-yl)-2-oxo-acetamide;

N-(5-oxo-2,5-dihydrofuran-3-yl)-2-(1-(3,4-dichlorobenzyl)-1H-indol-3-yl)-2-oxo-acetamide, m.p. >270° C.;

N-(5-oxo-2,5-dihydrofuran-3-yl)-2-(1-(3,4-dichlorobenzyl)-6-fluoro-1H-indol-3-yl)-2-oxo-acetamide;

N-(5-oxo-2,5-dihydrofuran-3-yl)-2-(1-(3,4-dichlorobenzyl)-6-methyl-1H-indol-3-yl)-2-oxo-acetamide;

N-(5-oxo-2,5-dihydrofuran-3-yl)-2-(1-(2-bromo-5-fluorobenzyl)-1H-indol-3-yl)-2-oxo-acetamide;

N-(5-oxo-2,5-dihydrofuran-3-yl)-2-(1-(2-fluoro-3-methylbenzyl)-1H-indol-3-yl)-2-oxo-acetamide;

N-(5-oxo-2,5-dihydrofuran-3-yl)-2-(1-(3-(methoxycarbonyl)benzyl)-1H-indol-3-yl)-2-oxo-acetamide; m.p. 248–250°C.;

N-(5-oxo-2,5-dihydrofuran-3-yl)-2-(1-(3,5-dibromobenzyl)-1H-indol-3-yl)-2-oxo-acetamide;

N-(5-oxo-2,5-dihydrofuran-3-yl)-2-(1-(4-fluoro-2-(trifluoromethyl)benzyl)-1H-indol-3-yl)-2-oxo-acetamide;

N-(5-oxo-2,5-dihydrofuran-3-yl)-2-(1-(2,3,6-trifluorobenzyl)-1H-indol-3-yl)-2-oxo-acetamide, m.p. 258–261° C.;

N-(5-oxo-2,5-dihydrofuran-3-yl)-2-(1-(2,4,5-trifluorobenzyl)-1H-indol-3-yl)-2-oxo-acetamide, m.p. 258–260° C.;

N-(5-oxo-2,5-dihydrofuran-3-yl)-2-(1-(2,4,6-trifluorobenzyl)-1H-indol-3-yl)-2-oxo-acetamide, m.p. 266–268° C.;

N-(5-oxo-2,5-dihydrofuran-3-yl)-2-(1-(2,3,4-trifluorobenzyl)-1H-indol-3-yl)-2-oxo-acetamide, m.p. 217–220° C.;

N-(5-oxo-2,5-dihydrofuran-3-yl)-2-(1-(4-trifluoromethoxybenzyl)-1H-indol-3-yl)-2-oxo-acetamide, m.p. 250–252° C.;

N-(5-oxo-2,5-dihydrofuran-3-yl)-2-(1-(4-trifluoromethoxybenzyl)-6-carbomethoxy-1H-indol-3-yl)-2-oxo-acetamide;

N-(5-oxo-2,5-dihydrofuran-3-yl)-2-(1-(3-trifluoromethoxybenzyl)-1H-indol-3-yl)-2-oxo-acetamide;

N-(5-oxo-2,5-dihydrofuran-3-yl)-2-(1-(2-biphenylmethyl)-1H-indol-3-yl)-2-oxo-acetamide;

N-(5-oxo-2,5-dihydrofuran-3-yl)-2(1-(4-difluoromethoxybenzyl)-1H-indol-3-yl)-2-oxo-acetamide;

N-(5-oxo-2,5-dihydrofuran-3-yl)-2-(1-(3,4-dimethoxy-6-nitrobenzyl)-1H-indol-3-yl)-2-oxo-acetamide;

N-(5-oxo-2,5-dihydrofuran-3-yl)-2-(1-(3-methoxybenzyl)-1H-indol-3-yl)-2-oxo-acetamide;

N-(5-oxo-2,5-dihydrofuran-3-yl)-2-(1-(2-chloro-4-fluorobenzyl)-1H-indol-3-yl)-2-oxo-acetamide;

N-(5-oxo-2,5-dihydrofuran-3-yl)-2-(1-(2,5-dichlorobenzyl)-1H-indol-3-yl)-2-oxo-acetamide;

N-(5-oxo-2,5-dihydrofuran-3-yl)-2-(1-(4-fluorobenzyl)-4-chloro-1H-indol-3-yl)-2-oxo-acetamide;

N-(5-oxo-2,5-dihydrofuran-3-yl)-2-(1-(4-fluorobenzyl)-5-chloro-1H-indol-3-yl)-2-oxo-acetamide;

N-(5-oxo-2,5-dihydrofuran-3-yl)-2-(1-(4-fluorobenzyl)-6-chloro-1H-indol-3-yl)-2-oxo-acetamide;

N-(5-oxo-2,5-dihydrofuran-3-yl)-2-(1-(4-fluorobenzyl)-2-methyl-1H-indol-3-yl)-2-oxo-acetamide;

N-(5-oxo-2,5-dihydrofuran-3-yl)-2-(1-(4-fluorobenzyl)-5-nitro-1H-indol-3-yl)-2-oxo-acetamide;

N-(5-oxo-2,5-dihydrofuran-3-yl)-2-(1-(4-fluorobenzyl)-6-fluoro-1H-indol-3-yl)-2-oxo-acetamide;

N-(5-oxo-2,5-dihydrofuran-3-yl)-2-(1-[4-fluorobenzyl]-5-chloro-1H-indol-3-yl)-2-oxo-acetamide;

N-(5-oxo-2,5-dihydrofuran-3-yl)-2-(1-(4-fluorobenzyl)-5-methoxy-1H-indol-3-yl)-2-oxo-acetamide;

N-(5-oxo-2,5-dihydrofuran-3-yl)-2-(1-(4-fluorobenzyl)-4-methyl-1H-indol-3-yl)-2-oxo-acetamide;

N-(5-oxo-2,5-dihydrofuran-3-yl)-2-(1-(4-fluorobenzyl)-5-methyl-1H-indol-3-yl)-2-oxo-acetamide;

N-(5-oxo-2,5-dihydrofuran-3-yl)-2-(1-(4-fluorobenzyl)-6-methyl-1H-indol-3-yl)-2-oxo-acetamide;

N-(5-oxo-2,5-dihydrofuran-3-yl)-2-(1-(4-fluorobenzyl)-7-methyl-1H-indol-3-yl)-2-oxo-acetamide;

N-(5-oxo-2,5-dihydrofuran-3-yl)-2-(1-(3-chlorobenzyl)-5-cyano-1H-indol-3-yl)-2-oxo-acetamide;

N-(5-oxo-2,5-dihydrofuran-3-yl)-2-(1-(4-biphenylmethyl)-6-carbomethoxy-1H-indol-3-yl)-2-oxo-acetamide;

N-(5-oxo-2,5-dihydrofuran-3-yl)-2-(1-(4-methoxybenzyl)-4-chloro-1H-indol-3-yl)-2-oxo-acetamide;

N-(5-oxo-2,5-dihydrofuran-3-yl)-2-(5-acetylamino-1-benzyl-1H-indol-3-yl)-2-oxo-acetamide;

N-(5-oxo-2,5-dihydrofuran-3-yl)-2-(6-fluoro-1-[(4-methylsulfonyl)benzyl]-1H-indol-3-yl)-2-oxo-acetamide;

N-(5-oxo-2,5-dihydrofuran-3-yl)-2-(1-methyl-6-methoxy-1H-indol-3-yl)-2-oxo-acetamide;

N-(5-oxo-2,5-dihydrofuran-3-yl)-2-(5-chloro-1-(4-methoxybenzyl)-2-methyl-1H-indol-3-yl)-2-oxo-acetamide;

N-(5-oxo-2,5-dihydrofuran-3-yl)-2-(5,6-methylenedioxy-1-(4-fluorobenzyl)-1H-indol-3-yl)-2-oxo-acetamide;

N-(5-oxo-2,5-dihydrofuran-3-yl)-2-(1-(4-pyridylmethyl)-1H-indol-3-yl)-2-oxo-acetamide, m.p. 210–212° C.;

N-(5-oxo-2,5-dihydrofuran-3-yl)-2-(1-(4-pyridylmethyl)-6-chloro-1H-indol-3-yl)-2-oxo-acetamide;

2-[1-(4-cyanobenzyl)-1H-indol-3-yl]-2-oxo-N-(5-oxo-2,5-dihydro-3-furanyl)acetamide, m.p. >260° C.;

2-[6-bromo-1-(4-chlorobenzyl)-1H-indol-3-yl]-2-oxo-N-(5-oxo-2,5-dihydro-3-furanyl)acetamide, m.p. 268–270° C.;

1-(4-chlorobenzyl)-3-{oxo[(5-oxo-2,5-dihydro-3-furanyl) amino]acetyl}-1H-indole-6-carboxylic acid, m.p. >300° C. (obtained by reaction of the corresponding 6-methoxycarbonyl derivative with three molar equivalents of 1N NaOH in 1-methyl-2-pyrrolidinone at room temperature overnight, followed by acidification at pH 1 with concentrated HCl);

2-{1-[(3,5-dimethyl-4-isoxazolyl)methyl]-1H-indol-3-yl}-2-oxo-N-(5-oxo-2,5-dihydro-3-furanyl)acetamide, m.p. 295–297° C.;

2-[1-(3-nitrobenzyl)-1H-indol-3-yl]-2-oxo-N-(5-oxo-2,5-dihydro-3-furanyl)acetamide, m.p. 257–260° C.;

2-[1-(2,5-difluorobenzyl)-1H-indol-3-yl]-2-oxo-N-(5-oxo-2,5-dihydro-3-furanyl)acetamide, m.p. 272–275° C.;

2-[1-(5-chloro-2-fluorobenzyl)-1H-indol-3-yl]-2-oxo-N-(5-oxo-2,5-dihydro-3-furanyl)acetamide, m.p. 285–287° C.;

2-[1-(4-tert-butylbenzyl)-1H-indol-3-yl]-2-oxo-N-(5-oxo-2,5-dihydro-3-furanyl)acetamide, m.p. 218–220° C.

ethyl 4-[(3-{oxo[(5-oxo-2,5-dihydro-3-furanyl)amino]acetyl}-1H-indol-1-yl)methyl]benzoate, m.p. 158–160° C.;

2-[1-(4-chlorobenzyl)-7-fluoro-1H-indol-3-yl]-2-oxo-N-(5-oxo-2,5-dihydro-3-furanyl)acetamide, m.p. 260–263° C.;

ethyl {4-[(3-{oxo[(5-oxo-2,5-dihydro-3-furanyl)amino]acetyl}-1H-indol-1-yl)methyl]phenyl}acetate, m.p. 228–230° C.;

2-(1-{[2-(dimethylamino)-2-oxoethyl]benzyl}-1H-indol-3-yl)-2-oxo-N-(5-oxo-2,5-dihydro-3-furanyl)acetamide, m.p. 228–229° C.;

benzyl {4-[(3-{oxo[(5-oxo-2,5-dihydro-3-furanyl)amino]acetyl}-1H-indol-1-yl)methyl]phenyl}acetate, m.p. 204–205° C.;

2-[1-(4-methyl-3-nitrobenzyl)-1H-indol-3-yl]-2-oxo-N-(5-oxo-2,5-dihydro-3-furanyl)acetamide, m.p. 238–240° C.;

{[3-(5-oxo-2,5-dihydro-furan-3-ylaminooxalyl)-indol-1-ylmethyl]-phenyl}-acetic acid tert-butyl ester, m.p. 195–198° C.;

1-(4-chlorobenzyl)-3-(5-oxo-2,5-dihydro-1-3-ylaminooxalyl)-1H-indole-4-carboxylic acid tert-butyl ester, m.p. 278° C.;

2-{1-[4-(benzyloxy)benzyl]-1H-indol-3-yl}-2-oxo-N-(5-oxo-2,5-dihydro-3-furanyl)acetamide, m.p. 258–260° C.;

2-[1-(4-chlorobenzyl)-4-cyano-1H-indol-3-yl]-2-oxo-N-(5-oxo-2,5-dihydro-3-furanyl)acetamide, m.p. >250° C.;

(2E)-3-(1-(4-chlorobenzyl)-3-{oxo[(5-oxo-2,5-dihydro-3-furanyl)amino]acetyl}-1H-indol-4-yl)-2-propenoic acid tert-butyl ester, m.p. 240–242° C.;

2-[4-[(allyloxy)methyl]-1-(4-chlorobenzyl)-1H-indol-3-yl]-2-oxo-N-(5-oxo-2,5-dihydro-3-furanyl)acetamide, m.p. 157–160° C.

EXAMPLE 5

2-[1-(4-chlorobenzyl)-1H-indol-3-yl]-2-oxo-N-(5-oxo-2,5-dihydro-3-thienyl)acetamide A suspension of 4-amino-5H-thiophen-2-one of Preparation 5 (103 mg), powdered potassium carbonate (138 mg) and 2-(1-(4-chlorobenzyl)-1H-indol-3-yl)-2-oxo-acetyl chloride of Example 1 (334 mg) in 1,2-dimethoxyethane (5 ml) is stirred at room temperature for 2 h. After this time the reaction mixture is poured in water (50 ml) and the obtained precipitate is collected by filtration and thoroughly washed with water. The still wet solid is suspended in methanol and stirred for 30'. Filtration followed by drying at 40° C. under vacuum gives 2-[1-(4-chlorobenzyl)-1H-indol-3-yl]-2-oxo-N-(5-oxo-2,5-dihydro-3-thienyl)acetamide (280 mg).

m.p. 268–270° C.,

1H-NMR (DMSO-d6, ppm): 4.49 (s, 2H); 5.65 (s, 2H); 6.75 (s, 1H); 7.34 (m, 2H); 7.35 (m, 2H); 7.43 (m, 2H); 7.63 (m, 1H); 8.25 (m, 1H); 9.07 (s, 1H); 11.70 (s, 1H).

| Elemental analysis for $C_{21}H_{15}ClN_2O_3S$: | |
|---|---|
| % calculated: | C = 61.39, H = 3.68, N = 6.82, Cl = 8.63, S = 7.80 |
| % found: | C = 61.26, H = 3.70, N = 6.75, Cl = 8.56, S = 7.72 |

In a similar way the following compound is prepared:

2-[1-(4-fluorobenzyl)-1H-indol-3-yl]-2-oxo-N-(5-oxo-2,5-dihydro-3-thienyl)acetamid m.p. 248–250° C.;

EXAMPLE 6

2-[1-(4-chlorobenzyl)-1H-indol-3-yl]-N-methyl-2-oxo-N-(5-oxo-2,5-dihydro-3-furanyl)acetamide.

Under nitrogen atmosphere, sodium hydride (10 mg of a 60% wt/wt suspension in mineral oil) is added to a solution of 2-[1-(4-chlorobenzyl)-1H-indol-3-yl]-2-oxo-N-(5-oxo-2,5-dihydro-3-furanyl)acetamide (100 mg) in dry DMF (2 ml). After 20', methyl iodide (0.016 ml) is added. After 3 h the solvent is removed by roto-evaporation and the obtained residue is partitioned between water and ethyl acetate. The organic layer is dried over sodium sulfate and concentrated to dryness. The obtained residue is suspended in boiling MeOH/i-PrOH 1/1. After cooling to room temperature the insoluble material is collected by filtration and oven-dried at 60° C. for 3 h, to give 2-[1-(4-chlorobenzyl)-1H-indol-3-yl]-N-methyl-2-oxo-N-(5-oxo-2,5-dihydro 3-furanyl)acetamide (52 mg).

m.p. 205–208° C.

1H-NMR (DMSO-d6, ppm): 3.27 (s, 3H), 5.44 (s, 2H); 5.56 (s, 2H); 5.87 (s, 1H); 7.25–7.47 (m, 6H); 7.55–7.69 (m, 1H); 8.09–8.22 (m, 1H); 8.64 (s, 1

| Elemental analysis for $C_{22}H_{17}N_2O_4$: | |
|---|---|
| % calculated: | C = 64.63, H = 4.19, N = 6.85 |
| % found: | C = 64.42, H = 4.22, N = 6.82 |

EXAMPLE 7

{4-[(3-{oxo[(5-oxo-2,5-dihydro-3-furanyl)amino]acetyl}-1H-indol-1-yl)methyl]phenyl}acetic acid A solution of benzyl {4-[(3-{oxo[(5-oxo-2,5-dihydro-3-furanyl)amino]acetyl}-1H-indol-1-yl)methyl]phenyl}acetate (300 mg) in DMF (10 ml) is hydrogenated at room temperature and pressure in the presence of 10% palladium on charcoal (60 mg of a 50% wt/wt suspension in water). After 3 h30' the catalyst is removed by filtration and the filtrate is concentrated to dryness. The residue obtained is suspended in absolute ethanol and recovered by filtration, to give {4-[(3-{oxo[(5-oxo-2,5-dihydro-3-furanyl)amino]acetyl}-1H-indol-1-yl)methyl]phenyl}acetic acid (160 mg).

m.p. >270° C.

1H-NMR (DMSO-d6, ppm): 3.55 (s, 2H), 5.13 (s, 2H); 5.60 (s, 2H); 6.05 (s, 1H); 7.20–7.40 (m, 6H); 7.65 (m, 1H); 8.30 (m, 1H); 9.05 (s, 1H); 11.88 (br.s, 1H), 12.25 (br. s, 1H).

| Elemental analysis for $C_{23}H_{18}N_2O_6$: | |
|---|---|
| % calculated: | C = 66.02, H = 4.34, N = 6.70 |
| % found: | C = 65.99, H = 4.39, N = 6.68 |

Using a similar procedure, the following compound is prepared by catalytic hydrogenation of 2-{1-[4-(benzyloxy)benzyl]-1H-indol-3-yl}-2-oxo-N-(5-oxo-2,5-dihydro-3-furanyl)acetamide:

2-[1-(4-hydroxybenzyl)-1H-indol-3-yl]-2-oxo-N-(5-oxo-2,5-dihydro-3-furanyl)acetamide m.p. 303–305° C.

EXAMPLE 8

1-(4-chlorobenzyl)-3-(5-oxo-2,5-dihydro-furan-3-ylaminooxalyl)-1H-indole-4-carboxylic acid Trifluoroacetic acid (0.2 ml) is added to a solution of 1-(4-chlorobenzyl)-3-(5-oxo-2,5-dihydro-furan-3-ylaminooxalyl)-1H-indole-4-carboxylic acid tert-butyl ester (200 mg) in $CH_2Cl_2$. After stirring at room temperature for 4 h, an additional amount of trifluoroacetic acid is added (0.2 ml) and the reaction mixture is stirred overnight. After roto-evaporation, the residue obtained is suspended in ethyl acetate under stirring and the solid is then recovered by filtration, to give 1-(4-chloro-benzyl)-3-(5-oxo-2,5-dihydro-furan-3-ylaminooxalyl)-1H-indole-4-carboxylic acid (120 mg).

m.p. 279° C.

| Elemental analysis for $C_{22}H_{15}ClN_2O_6$: | |
|---|---|
| % calculated: | C = 66.21, H = 3.45, N = 6.38, Cl = 8.08 |
| % found: | C = 59.51, H = 3.47, N = 6.22, Cl = 7.88 |

Using a similar procedure, the following compound is prepared staring from (2E)-3-(1-(4-chlorobenzyl)-3-{oxo[(5-oxo-2,5-dihydro-3-furanyl)amino]acetyl}-1H-indol-4-yl)-2-propenoic acid tert-butyl ester:

(2E)-3-(1-(4-chlorobenzyl)-3-{oxo[(5-oxo-2,5-dihydro-3-furanyl)amino]acetyl}-1H-indol-4-yl)-2-propenoic acid, m.p. >250° C.

EXAMPLE 9

1-(4-chlorobenzyl)-N-[2-(dimethylamino)ethyl]-3-{oxo[(5-oxo-2,5-dihydro-3-furanyl)amino]acetyl}-1H-indole-4-carboxamide Under a nitrogen atmosphere, 1-(3-dimethylaminopropyl)-3-ethylcarbodiimide hydrochloride (44 mg) is added to a stirred solution of 1-(4-chlorobenzyl)-3-(5-oxo-2,5-dihydro-furan-3-ylaminooxalyl)-1H-indole-4-carboxylic acid (50 mg) and N,N-dimethylethylenediamine (0.014 ml) in dry DMF (1 ml). After stirring at room temperature for 4 h, the reaction mixture is concentrated to dryness by roto-evaporation and the residue is taken up in water. The solid material is collected by filtration and thoroughly washed with water, to give 1-(4-chlorobenzyl)-N-[2-(dimethylamino)ethyl]-3-{oxo[(5-oxo-2,5-dihydro-3-furanyl)amino]acetyl}-1H-indole-4-carboxamide (49 mg).

m.p. 225–227° C.

| Elemental analysis for $C_{26}H_{25}ClN_4O_5$: | |
|---|---|
| % calculated: | C = 61.36, H = 4.95, N = 11.01, Cl = 6.97 |
| % found: | C = 61.28, H = 5.02, N = 11.02, Cl = 6.90. |

Using a similar procedure, the following compounds are obtained by reaction of 1-(4-chlorobenzyl)-3-(5-oxo-2,5-dihydro-furan-3-ylaminooxalyl)-1H-indole-4-carboxylic acid with N-(tert-butoxycarbonyl)ethylenediamine or with diethylamine:

tert-butyl 2-{[(1-(4-chlorobenzyl)-3-{oxo[(5-oxo-2,5-dihydro-3-furanyl)amino]-acetyl}-1H-indol-4-yl)carbonyl]amino}ethylcarbamate;

1-(4-chlorobenzyl)-N,N-diethyl-3-{oxo[(5-oxo-2,5-dihydro-3-furanyl)amino]acetyl}-1H-indole-4-carboxamide, m.p. 218–219° C.

EXAMPLE 10

N-(2-aminoethyl)-1-(4-chlorobenzyl)-3-{oxo [(5-oxo-2,5-dihydro-3-furanyl)amino]acetyl}-1H-indole-4-carboxamide Trifluoroacetic acid (0.1 ml) is added to a stirred solution of tert-butyl 2-{[(1-(4-chlorobenzyl)-3-{oxo[(5-oxo-2,5-dihydro-3-furanyl)amino]acetyl}-1H-indol-4-yl)carbonyl]amino}ethylcarbamate of Example 9 (50 mg) in $CH_2Cl_2$ (1 ml). After stirring at room temperature for 3 h the solvent is removed by roto-evaporation and the residue is taken up with water, adjusting the pH at about 8–9 with 1N NaOH. The precipitate is collected by filtration and thoroughly washed to give N-(2-aminoethyl)-1-(4-chlorobenzyl)-3-{oxo[(5-oxo-2,5-dihydro-3-furanyl)amino]acetyl}-1H-indole-4-carboxamide (25 mg).

m.p. 190–196° C.

EXAMPLE 11

2-[1-(4-chlorobenzyl)-4-(hydroxymethyl)-1H-indol-3-yl]-2-oxo-N-(5-oxo-2,5-dihydro-3-furanyl)acetamide 2-[4-[(allyloxy)methyl]-1-(4-chlorobenzyl)-1H-indol-3-yl]-2-oxo-N-(5-oxo-2,5-dihydro-3-furanyl)acetamide (239 mg) is dissolved in $MeOH/H_2O=9/1$ (10 ml) then 10% Pd/C (12 mg) and p-toluenesulfonic acid (12 mg) are added. The reaction is refluxed for about 6 h, then it is diluted with DMF and EtOH, the catalyst is filtered on celite and the solvent is removed under reduced pressure. The crude is washed with acetone and filtered. The filtrate is concentrated and the obtained solid is purified by silica gel chromatography (eluent: $CH_2Cl_2/EtOH=95/5$) affording 50 mg of pure 2-[1-(4-chlorobenzyl)-4-(hydroxymethyl)-1H-indol-3-yl]-2-oxo-N-(5-oxo-2,5-dihydro-3-furanyl)acetamide. The solid is crystallized from $CH_3CN$ affording 63 mg of compound with m.p. 238–240° C.

1H-NMR (DMSO): 11.78 (bs, 1H), 8.89 (s, 1H), 7.49-7.29 (m, 7H), 6.02 (s, 1H), 5.63 (s, 2H), 5.15 (s, 2H), 5.10 (d, 2H, J 6.0 Hz), 4.89 (t, 1H, J 6.0 Hz).

EXAMPLE 12

Evaluation of the Antitumor Effect of the Compounds of the Invention

The compounds according to the invention have been pharmacologically tested against four human tumour cell lines: HT 29 (colon carcinoma), PC 3 (prostate carcinoma), H 460M (lung carcinoma), MKN45 (gastric carcinoma). Cells were incubated with the tested compound for 144 hours, then cytotoxicity was determined by using the MTT assay (Mosman, T. "Rapid Colorimetric Assay for Cellular Growth and Survival: Application to Proliferation and Cytotoxicity Assay"; J. Immunolog. Methods, (1983), 65, 66; Green, L. M., "Rapid Colorimetric Assay for Cell Viability; Application to the Quantitation of Cytotoxic and Growth Inhibitory Lymphokines", J. Immunol. Methods, (1984), 70, 257–268).

The obtained data evidenced that the compounds of the invention have remarkable activity against solid tumors, in particular colon and lung tumors.

TABLE

Cytotoxic activity of representative compounds of the invention against human tumor lines.

| Structure | Example | HT29 (IC50, μg/ml) | PC3 (IC50, μg/ml) | H460M (IC50, μg/ml) | MKN-45 (IC50, μg/ml) |
|---|---|---|---|---|---|
| (indole with N-(4-chlorobenzyl), 3-oxoacetamide-furanone) | 2 | 0.13 | 0.22 | 0.011 | 0.048 |
| (indole with N-(4-fluorobenzyl), 3-oxoacetamide-furanone) | 3 | 0.0004 | 0.035 | 0.012 | 0.088 |
| (6-chloroindole with N-(4-chlorobenzyl), 3-oxoacetamide-furanone) | 4 | 0.1 | 0.3 | 0.049 | 0.12 |

HT29: Human colon adenocarcinoma
PC3: Human prostate carcinoma
H460M: Human lung carcinoma
MKN-45: Human gastric carcinoma

What is claimed is:

1. Compounds of formula I

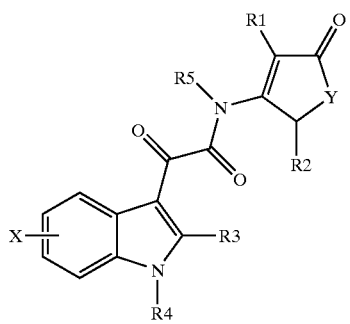

wherein:
- R1, R2 and R5 are independently hydrogen or a C1–C6 alkyl group;
- R3 is hydrogen, C1–C4 alkyl, aralkyl, optionally substituted phenyl;
- R4 is hydrogen, straight or branched C1–C8 alkyl, C5–C6 cycloalkyl; aralkyl; heteroaralkyl;
- X is one or more groups, at most four, independently selected from hydrogen C1–C6 alkyl; C1–C6 haloalkyl; C1–C6 hydroxyalkl; C1–C6-aminoalkyl; C1–C6-alkoxy-C1–C6-alkyl; C1–C1–C18-acyloxy-C1–C6-alkyl; hydroxy; C1–C4 alkoxy; C1–C3 haloalkoxy; phenoxy; aralkoxy; C1–C3 acyloxy; amino; C1–C3 alkylamino; C1–C3-acylamino; C1–C3-alkylsulfonylamino; aroylamino; halogen; nitro; cyano; trifluoromethyl; carboxy; C1–C6 alkoxycarbonyl; a RaRbN(CH$_2$)$_n$C(=O)— group wherein Ra and Rb are independently hydrogen, C1–C3-alkyl and n=0 or an integer from 1 to 4; a RaRcN(CH$_2$)$_n$C(=O)— group wherein Ra and n are as above defined and Rc is a C1–C4-alkoxycarbonyl group; a R1C(=O)— group wherein R1 is as above defined; sulfonyl; mercapto; C1–C4-alkylthio; C1–C4-alkylsulfinyl; C1–C4-alkylsulfonyl; aminosulfonyl; C1–C3-alkylaminosulfonyl; a group —P(=O)(OR1)(OR2) being R1 and R2 as above defined; a group (E)— or (Z)—C(R1)=C(R2)—C(=O)R6 wherein R6 is hydroxy, C1–C6-alkoxy, NRaRb or a group of formula RaRbN(CH$_2$)$_m$NR1—, being m an integer from 2 to 4 and R1, R2, Ra, and Rb as above defined;
- Y is an oxygen atom, the isomers, enantiomers and mixtures thereof, and the pharmaceutically acceptable salts thereof.

2. Compounds as claimed in claim 1 wherein R1, R2 and R3 are hydrogen or methyl.

3. Compounds as claimed in claim 1 wherein R4 is hydrogen; methyl; benzyl substituted on the benzene ring with one or more groups selected form methyl, t-butyl, fluorine, chlorine, bromine, hydroxy, acetoxy, methoxy, trifluoromethoxy, benzyloxy, trifluoromethyl, cyano, nitro, amino, acetylamino, methylsulfonylamino, methylmercapto, methylsulfinyl, methylsulfonyl, phenyl, ethoxycarbonyl, carboxy, carboxymethyl, (ethoxycarbonyl)methyl, (tert-butoxycarbonyl)methyl, (benzyloxycarbonyl)methyl, (dimethylcarbamoyl)methyl; α-naphthyl, β-naphthyl; 4-pyridyl; 4-pyridyl-N oxide.

4. Compounds as claimed in claim 1 wherein X is methyl, ethyl, fluorine, chlorine, bromine, hydroxy, acetoxy, methoxy, phenoxy, trifluoromethoxy, trifluoromethyl, cyano, nitro, amino, acetylamino, methylsulfonylamino, methylmercapto, methylsulfinyl, methylsulfonyl, carboxy, methoxycarbonyl, tert-butoxycarbonyl, diethylcarbamoyl, (2-aminoethyl)carbamoyl, (2-dimethylaminoethyl)carbamoyl, (E)— and (Z)-2---carboxyethen-1-yl, (E)— and (Z)—(2-tert-butoxycarbonyl)ethen-1-yl, (E)— and (Z)—(ethoxycarbonyl)ethenyl, hydroxymethyl, and allyloxymethyl.

5. Pharmaceutical compositions containing a compound of claim 1 in mixture with an acceptable carrier.

* * * * *